United States Patent [19]
Zukowski et al.

[11] Patent Number: 5,397,705
[45] Date of Patent: Mar. 14, 1995

[54] MULTIPLY MUTATED SUBTILISINS

[75] Inventors: Mark M. Zukowski, Thousand Oaks; Linda O. Narhi, Moorpark; Michael Levitt, Stanford, all of Calif.

[73] Assignee: Amgen Inc., Thousand Oaks, Calif.

[21] Appl. No.: 857,714

[22] Filed: Mar. 25, 1992

Related U.S. Application Data

[63] Continuation of Ser. No. 353,124, May 17, 1989, abandoned.

[51] Int. Cl.⁶ .................. C12N 9/54; C12N 9/56; C12N 15/00; C12N 15/57
[52] U.S. Cl. .................. 435/222; 435/69.1; 435/220; 435/221; 435/252.31; 435/320.1; 252/174.12; 536/23.2
[58] Field of Search .............. 435/222, 221, 69.1, 435/252.31, 172.3; 536/23.2

[56] References Cited

U.S. PATENT DOCUMENTS

| | | |
|---|---|---|
| 4,760,025 | 7/1988 | Estell et al. ............ 435/222 |
| 4,914,031 | 4/1990 | Zukowski et al. ........ 435/222 |
| 4,980,288 | 12/1990 | Bryan et al. ........... 435/222 |
| 4,990,452 | 2/1991 | Bryan et al. ........... 435/222 |
| 5,013,657 | 5/1991 | Bryan et al. ........... 435/172.3 |
| 5,155,033 | 10/1992 | Estell et al. ........... 435/221 |

FOREIGN PATENT DOCUMENTS

| | | |
|---|---|---|
| 0251446 | 1/1988 | European Pat. Off. ...... 435/222 |
| 0260105 | 3/1988 | European Pat. Off. ...... 435/172.3 |
| 0283075 | 9/1988 | European Pat. Off. ...... 435/222 |
| 08028 | 10/1988 | WIPO . |
| 8808614 | 10/1988 | WIPO . |

OTHER PUBLICATIONS

Kwon, S.-T., et al., 1988, (a) European Journal of Biochemistry, 173:491-497.
Kwon, S.-T., et al., 1988, (b) Journal of Biochemistry (Tokyo), 104:557-559.
Takagi, H., et al., 1990, The Journal of Biological Chemistry, 265(12):6874-6878.
Meloan, B., et al., 1985, FEBS Letters, 183(2):195-199.
Carter, P. and J. A. Wells, 1988; Nature, 332:564-568.
Estell, D. A., et al., 1986, Science 233:659-663.
Wells, J. A., et al., 1987, Proceedings of the National Academy of Sciences, USA 84:5167-5171.
Thomas, P. G., et al., 1985, Nature, 318:375-376.
Narhi, L. O., et al., 1988, Archives of Biochemistry and Biophysics, 261(1):161-169.
Siezen, R. J., et al., 1991, Protein Engineering, 4(7):719-737.

Primary Examiner—Robert A. Wax
Assistant Examiner—William W. Moore
Attorney, Agent, or Firm—Craig A. Crandall; Daniel M. Chambers; Steven M. Odre

[57] ABSTRACT

A class of subtilisin analogs suitable for admixture to cleaning compositions and having improved stability over naturally occurring Bacillus subtilisins are prepared by expressing a modified gene encoding the subtilisin analog in *Bacillus subtilis*.

17 Claims, 10 Drawing Sheets a = [Asp$^{76}$, Ser$^{109}$, Ser$^{218}$, Ala$^{222}$]-subtilisin and [Asp$^{76}$, Ser$^{109}$, Ser$^{218}$]-subtilisin incubated in 2% Chlorox and 1% SDS.

b = [Asp$^{76}$, Ser$^{109}$, Ser$^{218}$, Ala$^{222}$]-subtilisin incubated in 2% Chlorox.

c = [Asp$^{76}$, Ser$^{109}$, Ser$^{218}$]-subtilisin incubated in 2% Chlorox.

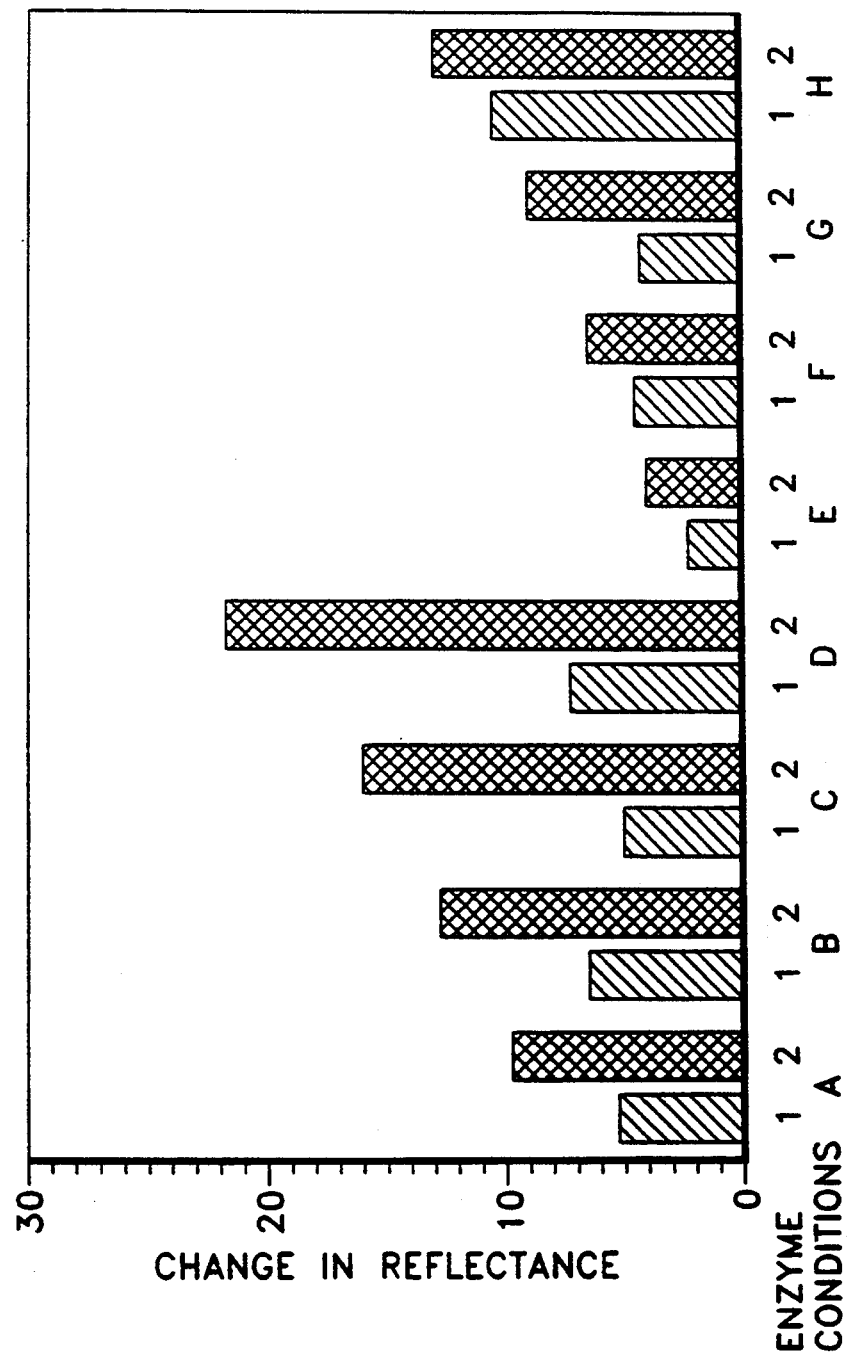

MULTIPLY MUTATED SUBTILISINS

This is a continuation of application Ser. No. 07/353,124, filed on May 17, 1989, now abandoned.

The present invention provides a novel class of thermally stable and pH stable subtilisin analogs with improved oxidation stability and superior performance in cleaning soiled fabrics when added to a standard detergent formulation, and to a method for preparing such analogs. In particular, the present invention relates to a class of subtilisin analogs having a modified calcium binding site providing improved calcium binding capacity, and a deletion and/or replacement of either residue of Asn-Gly sequences present in the subtilisin and a modification of one or more methionine residues to improve oxidation stability. The present invention further relates to detergent compositions containing such subtilisins and to the use of such subtilisins and compositions in cleaning applications.

BACKGROUND OF THE INVENTION

The term subtilisin designates a group of extracellular alkaline serine proteases produced by various species of Bacilli. These enzymes are also referred to as Bacillus serine proteases, Bacillus subtilisins or bacterial alkaline proteases.

Bacillus subtilisin molecules are composed of a single polypeptide chain of either 274 residues (for subtilisin type Carlsberg produced by *Bacillus licheniformis* and for the subtilisin produced by *Bacillus subtilis* strain DY) or 275 residues (for subtilisin type BPN' produced by *Bacillus amyloliquefaciens*, the aprA gene product of *Bacillus subtilis*, and the subtilisin of *Bacillus mesentericus* and the subtilisin of *Bacillus subtilis var. amylosacchariticus*). When comparing amino acid sequences of subtilisin from different strains of Bacillus herein, the sequence of subtilisin BPN' is used as a standard. For example, based on an alignment of sequences that gives the highest degree of homology between subtilisin Carlsberg and subtilisin BPN' the serine at the active site of the former is referred to as serine 221, even though it is located at position 220 of the amino acid sequence. On the same basis, position 220 of the amino acid sequence of subtilisin Carlsberg may be said to "correspond" to position 221 of subtilisin BPN'. See e.g., Nedkov et al., *Hoppe-Seyler's Z. Physiol. Chem.*, 364, 1537–1540 (1983).

The X-ray structure of subtilisin BPN' [Wright, et al., *Nature*, 221, 235 (1969)] revealed that the geometry of the catalytic site of subtilisin, involving $Asp^{32}$, $His^{64}$ and $Ser^{221}$, is almost identical to that of the active site of mammalian serine proteases (e.g., chymotrypsin) involving the residues $Asp^{102}$, $His^{57}$, and $Ser^{195}$. However, the overall dissimilarities between Bacillus serine proteases and mammalian serine proteases indicate that these are two unrelated families of proteolytic enzymes.

In the family of Bacillus subtilisins complete amino acid sequences are available for six subtilisins: Carlsberg, [Smith, et al., *J. Biol. Chem.*, 243, 2184–2191 (1968)]; BPN' [Markland, et al., *J. Biol. Chem.*, 242, 5198–5211 (1967)]; the aprA gene product [Stahl, et al., *J. Bacteriol.*, 158, 411–418 (1984)]; DY [Nedkov, et al., supra]; *Bacillus mesentericus* [Svendsen, et al., *FEBS Letters*, 196, 220–232 (1986), and *Bacillus subtilis var. amylosacchariticus* [Yoshimoto, et al., *J. Biochem.*, 103, 1060–1065 (1988)]. Subtilisin Carlsberg and subtilisin BPN' (sometimes referred to as subtilisin Novo) differ by 84 amino acids and one additional residue in BPN' (subtilisin Carlsberg lacks an amino acid residue corresponding to residue 56 of subtilisin BPN'). Subtilisin DY comprises 274 amino acids and differs from subtilisin Carlsberg in 32 amino acid positions and from subtilisin BPN' by 82 amino acid replacements and one deletion (subtilisin DY lacks an amino acid residue corresponding to residue 56 of subtilisin BPN'). The amino acid sequence of the aprA gene product is 85% homologous to the amino acid sequence of subtilisin BPN'. Thus, it appears that there is an extensive homology between amino acid sequences of subtilisins from different strains of Bacillus. This homology is complete in certain regions of the molecule and especially in those that play a role in the catalytic mechanism and in substrate binding. Examples of such sequence invariances are the primary and secondary substrate binding sites, $Ser^{125}$-$Leu^{126}$-$Gly^{127}$-$Gly^{128}$ and $Tyr^{104}$ respectively and the sequence around the reactive serine (221), $Asn^{218}$-$Gly^{219}$-$Thr^{220}$-$Ser^{221}$-$Met^{222}$-$Ala^{223}$.

Subtilisin molecules exhibit unique stability properties. Although they are not completely stable over a wide pH range, subtilisins are relatively resistant to denaturation by urea and guanidine solutions and their enzymatic activity is retained for some time in 8M urea. In solutions having a pH below 4, subtilisin rapidly and irreversibly loses its proteolytic activity. Gounaris, et al., *Compt. Rend. Tray. Lab. Carlsberg*, 35, 37 (1965) demonstrated that the acid deactivation of subtilisin is not due to a general charge effect and speculated that it is due to other changes in the molecule, such as protonation of histidine residues in the interior, hydrophobic parts of the molecule. Bacillus subtilisins undergo irreversible inactivation in aqueous solutions at a rate that is largely dependent upon temperature and pH. At pH values below 4 or above 11 the rate of inactivation is very rapid while at pH's of between 4.5 and 10.5 the rate, although much slower, increases as the solution becomes more alkaline. The mechanisms of this inactivation are not fully known but there is evidence indicating that autodigestion is responsible at least in part for enzyme instability at this pH range. In general, at any pH value, the higher the temperature the faster the rate of subtilisin deactivation.

The use of proteases in industrial processes which require hydrolysis of proteins has been limited due to enzyme instability under operational conditions. Thus, for example, the incorporation of trypsin into laundry detergents (e.g., Bio-38, Schnyder; Switzerland) to facilitate removal of proteinaceous stains had a very limited success which was undoubtedly a result of enzyme instability under the washing conditions. In addition, bacterial alkaline proteases compatible with detergents have been utilized in detergent formulations.

Because many industrial processes are conducted at temperatures that are above the stability range of most enzymes, highly thermostable proteases not only will be advantageous to certain industries such as detergent and hide dehairing, that already require stable proteases, but may be useful in industries that use chemical means to hydrolyze proteins e.g. hydrolysis of vegetable and animal proteins for the production of soup concentrates.

Although thermal inactivation may be the most important factor in restricting the industrial use of enzymes, other factors such as need for effectiveness over broad pH ranges and use of denaturing agents and oxidizing agents may also have a detrimental effect with respect to the use of proteases in industrial processes. It is therefore desirable to obtain a class of proteases characterized by improved stability with respect to temperature, pH, denaturing agents and oxidizing agents and other conditions required by various industries.

Over the past several years there have been major changes in detergent formulations, particularly in the replacement of phosphates with alternate builders and in the development of liquid laundry detergents to meet environmental and consumer demands. These changes create a need for changes in traditional detergent enzymes. More particularly, it has become desirable to employ proteolytic enzymes which possess greater storage stability in liquid laundry formulations as well as stability and activity at broader ranges of pH and temperature in a variety of commercial detergent formulations.

One approach to producing modified subtilisins useful in detergent formulations was disclosed in U.S. Pat. No. 4,760,025 wherein mutations in the subtilisin of *Bacillus amyloliquefaciens* (*B. amyloliquefaciens*) at positions $Asp^{32}$, $Asn^{155}$, $Tyr^{104}$, $Met^{222}$, $Gly^{166}$, $His^{64}$, $Gly^{169}$, $Phe^{189}$, $Ser^{33}$, $Tyr^{217}$ and/or $Gly^{157}$ were identified as providing changed stability, altered conformation or as having changes in the "processing" of the enzyme. In particular, a mutation of $Met^{222}$ to Ala or Ser assertedly resulted in improved oxidation stability, but the specific activity of the enzyme toward the synthetic peptide substrate, succinyl-L-alanyl-L-alanyl-L-prolyl-L-phenylalanyl-p-nitroanilide (sAAPFpN) was decreased when compared to the unmutated enzyme. It was suggested that substitution for $Gly^{166}$ with Ala, Asp, Glu, Phe, His, Lys, Asn, Arg or Val would alter the kinetic parameters of the enzyme. However, none of the mutations disclosed provide analogs having greater stability at high temperatures or stability over a broader pH range than the wild type enzyme.

In another approach, Thomas, et al, *Nature*, 318, 375-376 (1985), disclosed that the pH dependence of subtilisin may be altered by changing an Asp to Ser in $Asp^{99}$ of subtilisin BPN'. This change represents an alteration of a surface charge 14–15 Angstroms from the active site. However, Thomas, et al. fails to provide any indication of improvement where no change in surface charge is made, as is the case where one uncharged residue is substituted for another.

A third approach, described in International Application No. PCT/US87/00027, published as WO 87/04461, relates to a class of Bacillus serine protease analogs characterized by deletion and/or modifications of any Asn-Gly sequences present in the protease.

Takagi et al., J. Biol. Chem. 263, 19592–19596 (1988) disclose that a change of isoleucine 31 to leucine increases the activity of subtilisin compared to the wild-type enzyme.

SUMMARY OF THE INVENTION

The present invention provides a class of subtilisin analogs characterized as having improved pH and thermal stability and oxidation stability thereby rendering such analogs especially useful in detergent formulations as well as other processes requiring stable proteases. The subtilisin analogs according to the present invention are characterized as having an amino acid sequence of a naturally occurring Bacillus subtilisin that has been modified by having (1) one or more amino acid residues in a calcium binding site present in the amino acid sequence of the naturally occurring Bacillus subtilisin replaced with a negatively charged amino acid, and (2) either residue of any Asn-Gly sequence present in the amino acid sequence of the naturally occurring Bacillus subtilisin deleted or replaced and (3) one or more methionine residues replaced with another amino acid residue, preferably alanine or leucine and (4) one or more amino acid residues surrounding the catalytic triad ($Asp^{32}$ $His^{64}$, $Ser^{221}$) are replaced with another amino acid. The present invention further provides detergent compositions comprising the subtilisin analogs of the present invention and to the use of such subtilisin analogs and compositions in cleaning applications.

The subtilisin analogs of the present invention exhibit improved thermal, pH stability and oxidation stability, increased specific activity and broad substrate specificity thereby increasing the detergency of detergent formulations containing such analogs. In particular, the subtilisin analogs of the present invention provide improved thermostability, increased pH stability, increased oxidation stability and higher specific activity than found in "wild type" subtilisins.

In addition, the present invention relates to DNA sequences having codons encoding a subtilisin analog as described above.

The present invention also provides a process for the production of subtilisin analogs comprising a host cell having nucleic acid encoding a subtilisin analog as described above. In such a cell, the nucleic acid encoding the subtilisin analog may be chromosomal or extrachromosomal. The host cell is preferably selected from a strain deficient in secreted proteases, allowing for facile isolation of the analogs of the present invention.

In addition, the present invention provides a method for improving the thermal, pH, and oxidation stability of subtilisins by modifying the calcium binding site and/or substituting an amino acid other than asparagine for an asparagine in an Asn-Gly sequence and in particular for the asparagine residues at the positions in the amino acid sequence of the subtilisin which corresponds to positions 109 and 218 in the amino acid sequence as disclosed in Table 1, and substituting an amino acid other than methionine at the position in the amino acid sequence of the subtilisin which corresponds to positions 124 and 222 in the amino acid sequence as disclosed in Table 1, and substituting an amino acid other than the naturally occurring amino acid surrounding the active site of the enzyme.

BRIEF DESCRIPTION OF THE DRAWINGS

FIGS. 9 and 10 show the washing performance of [Asp$^{76}$, Ser$^{109}$ Ser$^{218}$, Ala$^{222}$] subtilisin.

DETAILED DESCRIPTION OF THE INVENTION

Figure 1:
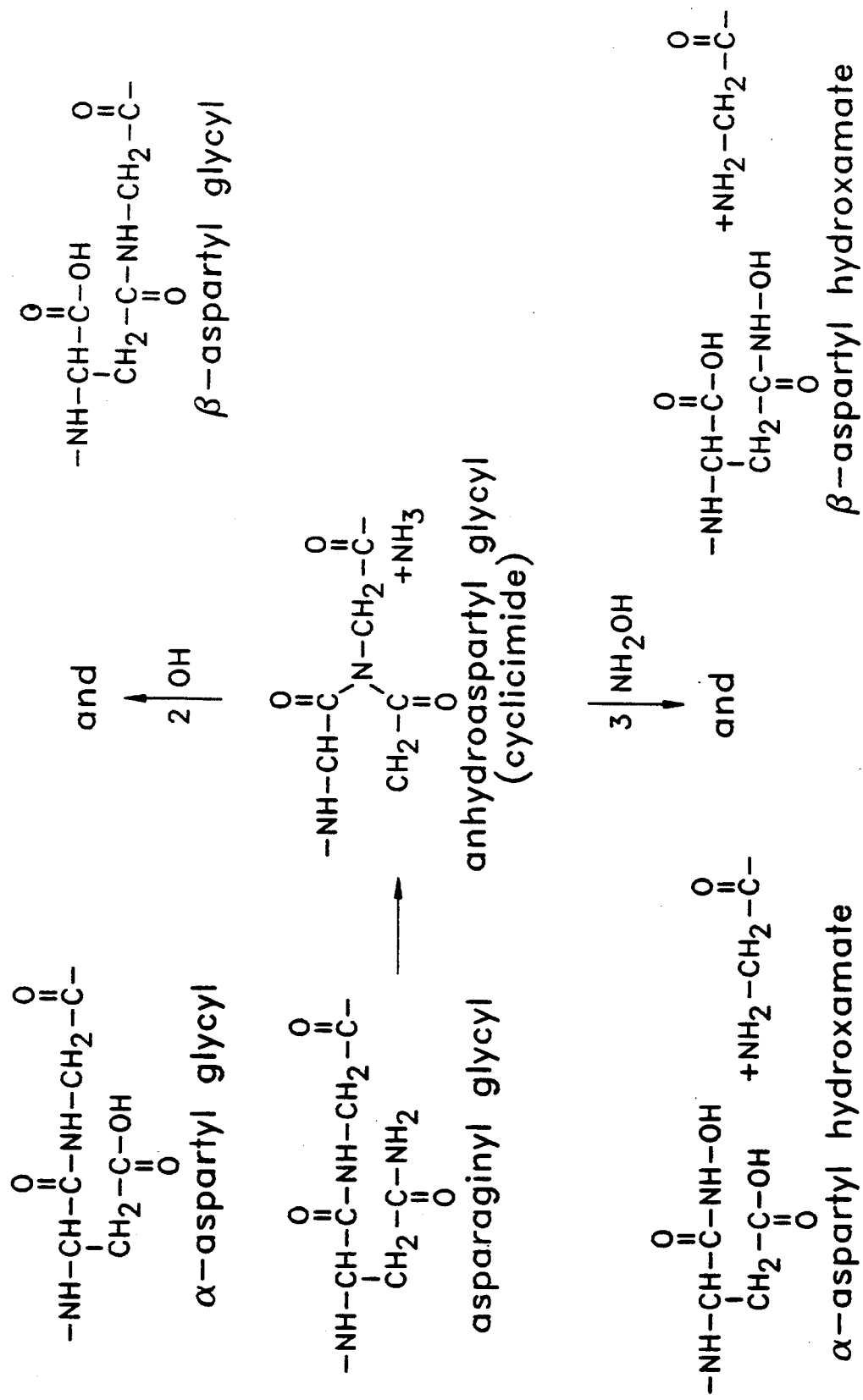
FIG. 1 schematically illustrates the cyclization of Asn-Gly residues, such as those found at positions 218 and 219 of subtilisin as set forth in Table 1, to form anhydroaspartylglycine and also depicts base-catalyzed hydrolysis thereof.

The term "subtilisin" as employed herein, refers to a mature, secreted form of the enzyme which lacks leader sequences cleaved from the mature enzyme prior to or at secretion. Subtilisins that may be modified in accordance with the present invention include, but are not limited to, naturally occurring subtilisins represented by the amino acid sequence of subtilisin Carlsberg, subtilisin BPN' the aprA gene product of *Bacillus subtilis*, subtilisin DY and the subtilisin of *Bacillus mesentericus*, and the subtilisin of *B. subtilis var. Amylosacchariticus*. The amino acid sequence for subtilisin Carlsberg is described by Smith, et al., *J. Biol. Chem.*, 243, 2184-2191 (1968). The amino acid sequence for subtilisin BPN' is described by Markland, et al., *J. Biol. Chem.*, 242, 5198-5211 (1967). The amino acid sequence for subtilisin DY is described by Nedlov, et al., *Hoppe-Seyler's Z. Physiol. Chem.*, 364, 1537-1540 (1983). The amino acid sequence for the subtilisin of *Bacillus mesentericus* is described by Svedsen, et al., FEBS Letters, 196, 220-232 (1986). The amino acid sequence for the subtilisin of *Bacillus subtilis var. amylosacchariticus* is described by Yoshimoto, et al., *J. Biochem.*, 103, 1060-1065 (1988). The amino acid sequence of the aprA gene product of *Bacillus subtilis* is described by Stahl, et al., *J. Bacteriol.*, 158, 411-418 (1984). The amino acid sequence of such subtilisins are incorporated by reference herein. Such subtilisins are characterized as having calcium binding sites necessary to stabilize the molecule.

In accordance with the present invention, a class of subtilisin analogs are provided which possess improved capacity to bind to calcium. Calcium has been used to stabilize subtilisin in powders and liquid detergent, especially in applications requiring higher temperatures. The present invention relates to the modification of the calcium binding site of the subtilisin molecule to increase calcium binding. As used herein the term "modification of the calcium binding site" refers to replacement of one or more amino acids in the region of a calcium binding site present in the amino acid sequence of subtilisin with a negatively charged amino acid thereby enabling the resulting subtilisin analog to have an additional negative charge. It has been found that one calcium binding site in a subtilisin involves the following amino acids: Gln2, Asp$^{41}$, Leu$^{75}$, Asn$^{76}$, Asn$^{77}$, Ser$^{78}$, Ile$^{79}$, Gly$^{80}$, Val$^{81}$, Thr$^{208}$ and Tyr$^{214}$ relative to the amino acid sequence set forth in Table 1. The present invention preferably involves replacement of one or more of the amino acids present in the calcium binding site with a "negatively charged" amino acid such as Asp and Glu, and more preferably Asp. It should be noted that although Asp$^{41}$ in the calcium binding site is a negatively charged amino acid, one embodiment of the present invention involves changing Asp$^{41}$ to Glu$^{41}$. The other embodiments relate to changes other than to Asp$^{41}$.

One preferred embodiment of the present invention involves a subtilisin analog wherein Asn$^{76}$ is converted to Asp$^{76}$. Another embodiment involves conversion of the Ile$^{79}$ to Asp$^{79}$. Another embodiment involves the above preferred modifications to the calcium binding site and substitutions of Asn$^{109}$ and Asn$^{218}$ to Ser$^{109}$ and Ser$^{218}$, thus eliminating two unstable Asn-Gly sequences. A more preferred embodiment of the present invention involves the above preferred modifications to the calcium binding site and Asn-Gly sequences in combination with changes of methionine 222 to alanine. Another preferred embodiment involves the above preferred modifications to the calcium binding site and Asn-Gly sequences and Met-222 in combination with amino acid modifications that increase the specificity of subtilisin to an azocasein substrate or a sAAPFpN substrate i.e., Methionine 124 to Leucine or Alanine and/or Isoleucine 31 to Leucine, and/or Serine 33 to Threonine, and/or Serine 62 to Asparagine, and/or Serine 63 to Glycine, and/or Tyrosine 217 to Leucine and/or Arginine 247 to Leucine or Methionine.

In addition to the calcium binding sites described above, subtilisins may have one or more additional calcium binding sites. The claims of the present invention encompass modification of one or more of all calcium binding sites that may be present in the subtilisin. The number of calcium binding sites in any particular subtilisin that may be modified depends on many factors, i.e., the specific subtilisin, the particular application for the subtilisin analog. Other potential calcium binding sites that may be present in subtilisins include the following (1) Asp$^{140}$ and Pro172; (2) Pro$^{14}$ and Gln271; and (3) Pro$^{172}$ and Glu$^{195}$ or Asp$^{197}$. The specific calcium binding site present in each molecule depends upon the particular subtilisin to be modified. As previously mentioned, the replacement of one or more of the amino acids in the above potential calcium binding sites will result in a subtilisin having improved thermal and pH stability. Representative of replacements include Asp$^{140}$ with Glu$^{140}$, Pro$^{172}$ with Asp$^{172}$, Pro$^{14}$ with Asp$^{14}$, Gln$^{271}$ with Glu$^{271}$, Glu$^{197}$ with Asp$^{197}$.

In addition to modifying the calcium binding sites of a subtilisin molecule, it is preferred to have any Asn-Gly sequence present in the subtilisin deleted or replaced. As previously disclosed in International Application No. PCT/US87/00027, supra, a conserved sequence, Asn-Gly, at positions 109-110 and especially at positions 218-219 of Bacillus subtilisins has been identified as a major factor responsible for the pH instability of these substances (see FIG. 1). In order to eliminate the unstable element, Asn$^{218}$-Gly$^{219}$, from the subtilisin molecule it was disclosed to either replace Asn$^{218}$ with any amino acid other than asparagine and/or change Gly$^{219}$ to any amino acid other than glycine. In a like manner, modification of the unstable Asn-Gly element at positions 109-110 was described as providing stability to the analogs described therein.

In addition, as previously noted, a preferred class of analogs of a Bacillus subtilisin according to the present invention have an amino acid sequence wherein in addition to a modification of a calcium binding site, positions comprising an Asn-Gly sequence in the Bacillus subtilisin do not comprise an Asn-Gly sequence in the analog, and in particular wherein there are fewer Asn-Gly sequences than in the Bacillus subtilisin. Most preferably, a position corresponding to position 218 in the amino acid sequence as set forth in Table 1, does not comprise an asparaginyl residue, but rather comprises a residue of a different amino acid, preferably an amino acid selected from among serine, valine, threonine, cysteine, glutamine and isoleucine. To the extent that replacement of asparagine with certain amino acids may give rise to interference with active site conformation, (e.g., due to steric hindrance which may be introduced by the presence of an aromatic amino acid or changes in tertiary structure such as may be introduced by the presence of a proline) substitution with such amino acids would ordinarily be less preferred. Likewise, to the extent that replacement of asparagine with other amino acids may introduce a charged group (e.g., aspartic acid) into the proximity of the active site, such substitution would be less preferred. Illustrative of a presently preferred embodiment is an analog having a modified calcium binding site and a [$Ser^{218}$] modification of the Asn-Gly sequence of the subtilisin. Alternative embodiments of analogs within the contemplation of the invention are those having a modified calcium binding site and wherein $Asn^{109}$ of subtilisin BPN' or of the aprA gene product is replaced, preferably by a serine, and wherein glycine residues at positions 110 and/or 219 are replaced by different amino acid residues. In other subtilisins, modification of a calcium binding site or sites and substitution for Asn at residue 62 or Gly at residue 63 of subtilisins Carlsberg or DY are also comprehended by the present invention.

In addition, as previously noted, a preferred class of analogs of a Bacillus subtilisin according to the present invention have an amino acid sequence wherein in addition to modifications at the calcium binding site(s) and Asn-Gly sequences, a Met residue at position 222 is replaced with a different amino acid, preferably Ala, to improve the oxidation stability of the subtilisin analog.

Alternative embodiments of analogs within the contemplation of the invention are substitutions of amino acids surrounding the active site residues ($Asp^{32}$, $His^{64}$ and $Ser^{221}$), so as to increase the specific activity of the enzyme toward azocasein and synthetic peptide (e.g., sAAPFpN) substrates. Such modifications are especially important in analogs incorporating a modification at $Met^{222}$ to Ala because, as previously noted, the $Met^{222}$ to Ala analog has a specific activity toward the sAAPFpN substrate that is less than that of the unmutated enzyme. The specific activity of any analog incorporating the $Met^{222}$ to Ala substitution can be increased by incorporating one or more of the following additional changes: $Met^{124}$ to Leu, $Met^{124}$ to Ala, $Ile^{31}$ to Leu, $Ser^{33}$ to Thr, $Ser^{62}$ to Asn, $Ser^{63}$ to Gly, $Tyr^{217}$ to Leu, $Arg^{247}$ to Leu or Met.

Due to their capacity to secrete substantial quantities of proteins and because they are currently used to produce detergent proteases, Bacillus microorganisms represent a preferred host for recombinant production of the subtilisin analogs according to the present invention. Because most Bacilli secrete alkaline and neutral proteases, it is preferable that mutations be introduced into the endogenous alkaline and neutral protease genes of B. subtilis so that the mutated subtilisin may be produced and secreted by B. subtilis in a medium free of other proteases. Thus the present invention also provides mutant strains of B. subtilis which are blocked with respect to the synthesis of endogenous proteases but which retain the ability to synthesize and secrete the subtilisin analogs herein disclosed.

As described in greater detail below, it was found that the pH and thermal stability and oxidation stability and the stability in detergent formulations of the subtilisin analogs of the present invention is significantly greater than that of the wild type aprA gene product subtilisin and Carlsberg subtilisin.

All subtilisin analogs according to the invention may be prepared in accordance with the following procedure:
1) Isolation of the representative subtilisin gene aprA from B. subtilis;
2) Cloning of the aprA gene on a vector which permits utilization of oligonucleotide site-directed mutagenesis to create desired modifications;
3) Site-directed mutagenesis and sequencing of the resulting DNA to confirm the presence of the desired mutation;
4) Construction of an expression vector to direct the synthesis of the mutated enzyme in B. subtilis;
5) Construction of mutated B. subtilis strains which do not synthesize subtilisin and neutral protease;
6) Practice of procedures for insertion of the gene coding for the improved enzyme into the chromosome of a B. subtilis strain previously mutated to block synthesis of endogenous proteases.
7) Isolation of the enzyme in the extracellular growth medium and its purification.

As used herein, the specific subtilisin analogs are indicated by representing the replacement amino acid in brackets. For example, a [$Ser^{109}$] subtilisin refers to a subtilisin molecule having a serine in amino acid position 109 and a [$Ser^{109}$, $Ser^{218}$] subtilisin refers to a subtilisin molecule having a serine at amino acid positions 109 and 218.

In Example 1, the aprA gene encoding subtilisin is isolated from the B. subtilis genome. In Example 2, the aprA gene is subjected to site-directed mutagenesis. In Example 3, an expression vector containing the mutated aprA gene is constructed. In Example 4, a [$Ser^{109}$] subtilisin analog is prepared. Example 5 describes the preparation of a [$Ser^{109}$, $Ser^{218}$] subtilisin analog. Example 6 describes preparation of a [$Asp^{76}$, $Ser^{109}$, $Ser^{218}$] subtilisin analog. Example 7 describes the preparation of a [$Asp^{76}$, $Glu^{79}$, $Ser^{109}$, $Ser^{218}$] subtilisin analog.

In Example 8, a [$Asp^{76}$, $Ser^{109}$, $Ser^{218}$ $Ala^{222}$] subtilisin analog is prepared. In Example 9, the [$Asp^{76}$, $Ser^{109}$, $Ser^{218}$, $Ala^{222}$] subtilisin analog gene is transferred to bacteriophage M13mp19 in preparation for site-directed mutagenesis. In Example 10, a [$Leu^{31}$, $Asp^{76}$, $Ser^{109}$, $Ser^{218}$, $Ala^{222}$] subtilisin analog is prepared. Example 11 describes the preparation of a [$Asp^{76}$, $Ser^{109}$, $Leu^{124}$, $Ser^{218}$, $Ala^{222}$] subtilisin analog.

In Example 12, two mutant strains of B. subtilis which produce no detectable extracellular proteases are constructed. Example 13 describes procedures for integration of a mutated aprA gene into the chromosome of B. subtilis. In Example 14, wild-type and mutant aprA subtilisins are isolated and purified. Examples 15, 16, 17, 18, and 19 describe characteristics of the subtilisin analogs of the present invention regarding stability, activity and washing performance.

In addition to a subtilisin analog of the present invention, detergent compositions of the present invention may comprise:
(a) At least one surfactant which may be anionic, non-ionic, or amphoteric, or a water-soluble soap. Typically, an anionic surfactant (e.g., a linear alkyl aryl sulphonate) is used in admixture with a non-ionic (e.g., an alkyl phenyl polyglycol ether) in amounts of 5-30 and 1-5 percent by weight, respectively, of the detergent composition.
(b) One or more builders, preferably having a concomitant sequestering function. Sodium tripolyphosphate, sodium citrate, sodium silicate, and zeolites are examples of such compounds, usually constituting from 10 to 70 percent by weight of the detergent composition.

(c) A bleaching agent, preferably a peroxy compound such as sodium perborate, typically incorporated in an amount up to 30 percent by weight of the composition.

(d) Ancillary agents, such as carboxymethyl cellulose, optical brighteners and perfumes. If required, a pH-adjusting agent is added to give a pH of the laundering medium in the range of from 7.0 to 10.5.

The detergent compositions contain an effective amount of one or more of the subtilisin analogs of the present invention. As used herein "effective amount of a subtilisin analog" refers to the quantity of subtilisin analog necessary to achieve the enzymatic activity necessary in the specific detergent composition. Such effective amounts are readily ascertained by one of ordinary skill in the art and is based on many factors, such as the particular subtilisin analog utilized, the cleaning application, the specific composition of the detergent composition, whether a liquid or dry composition is required and the like.

The particulate subtilisin analog preparation of the invention is added in an amount calculated to give an enzyme activity of at least 0.1 Anson units (AU, vide infra), preferably 0.5–2.5 AU per 100 g of detergent composition. If required, balance to 100 percent may be established with an inorganic filler, preferably sodium sulphate.

Liquid detergent compositions may be prepared from enzyme slurries, preferably in non-aqueous media. Typically, such slurries may consist of a suspension of finely ground subtilisin analog concentrate in a liquid non-ionic surfactant, for example Tergitol TM 15 S 9 or a mixture of such surfactants. Usually, the slurry will also contain one or more inorganic fillers, such as finely ground sodium chloride, optionally in admixture with a suspension stabilizer, for example fumed silica (Aerosil TM 1200). Tergitol and Aerosil are trademarks.

A subtilisin analog of the invention is added in an amount calculated to give a protease activity of at least 0.1 AU preferably 0.5–2.5 AU per 100 g of liquid detergent composition.

The detergent compositions may be prepared in the usual manner, for example by mixing together the components. Alternatively, a pre-mix is made, which is then mixed with the remaining ingredients.

Because of the good stability and activity properties described, the subtilisin analogs according to the invention can be used in all fields where proteolytic enzymes are generally used. In particular, it can be used for detergents and cleansers or spot removers, as a depilatory in tanning, and also in the food industry for the preparation of protein hydrolysates and in serology for the detection of incomplete antibodies. It is particularly advantageous for use in the food industry and in serology that the subtilisin analogs according to the invention have excellent stability in the solid or dissolved form that physiologically acceptable quantities of calcium ions may not be necessary to stabilize the subtilisin analog in aqueous solutions, in contrast to those of other enzyme preparations.

The following Examples will further serve to illustrate the invention although it will be understood that the invention is not limited to these specific examples.

EXAMPLE 1

*B. subtilis* strain QB127 (trpC2 leuA8 sacU$^h$200) [Lepesant, et al., *Molec. Gen. Genet.*, 118, 135–160 (1982)] was obtained from the Bacillus Genetic Stock Center at the Ohio State University, Columbus, Ohio. This strain overproduces extracellular serine and metal proteases, α-amylase and levansucrase relative to isogenic sacU+ strains due to the pleiotropic effect of the sacU$^h$200 mutation [Lepesant, et al., in Schlessinger, D., ed., *Microbiology*, 1976, American Society for Microbiology, Washington, D.C., p. 65 (1976)]. Thus, strain QB127 is a suitable source of DNA for isolating the aprA gene which codes for subtilisin.

Genomic DNA was isolated from cells of *B. subtilis* strain QB127 in accordance with the procedure of Saito, et al., *Biochim. Biophys. Acta.* 72, 619–629 (1963). Purified chromosomal DNA was digested to completion with the EcoRI restriction endonuclease.

The resulting DNA fragments were resolved on a low-melting point agarose gel by electrophoresis and fragments in the 4.4 to 8.0 kilobase (kb) range were isolated. These fragments were ligated to pCFM936 (A.T.C.C. No. 53,413 from the American Type Culture Collection, 12301 Parklawn Drive, Rockville, Md.) an *Escherichia coli* (*E. coli*) plasmid which displays higher copy numbers at elevated temperatures and which confers kanamycin resistance. The vector was digested with EcoRI and dephosphorylated with calf intestine alkaline phosphatase prior to ligation.

The ligation products were introduced into *E. coli* C600 ( A.T.C.C. No. 23724 from the American Type Culture Collection, 12301 Parklawn Drive, Rockville, Md.) and following overnight incubation on L-agar supplemented with 10 μg/ml kanamycin, kanamycin-resistant host cells were selected. Plasmid DNA was amplified by incubating the selected host cells at 42° C. for 4 hours. Colonies were then transferred to nitrocellulose filters and processed in accordance with a colony hybridization procedure described by Grunstein, et al., *Proc. Natl. Acad. Sci.* (*USA*), 72, 3961 (1975).

An oligonucleotide probe was used to screen for colonies which harbored the subtilisin gene on pCFM936. The probe synthesized by the phosphite method described by Beaucage, et al., *Tetrahedron Letters*, 22, 1859–1862 (1981) had the nucleotide sequence

5' GCGCAATCTGTTCCTTATGGC 3' which corresponds to the amino-terminus of the aprA gene product (Wong, et al., *Proc. Natl. Acad. Sci.* (*USA*), 81, 1184–1188 (1984); Stahl, et al., *J. Bacteriol.*, 158, 411–418 (1984). A hybridization temperature of 55° C. was employed and 5 positive colonies were identified out of a total of 400. The plasmid DNA from one of the positive colonies was designated pCFM936 apr2.

Plasmid pCFM936 apr2 was digested with EcoRI alone, with HindIII alone and with EcoRI and HindIII in combination. Sizes of EcoRI fragments of the subtilisin gene conformed to those described in Stahl, et al., supra, but several otherwise undescribed HindIII sites were discovered. As described herein in Example 3, two of the HindIII sites were utilized in the genetic manipulations of the subtilisin gene.

Figure 2:
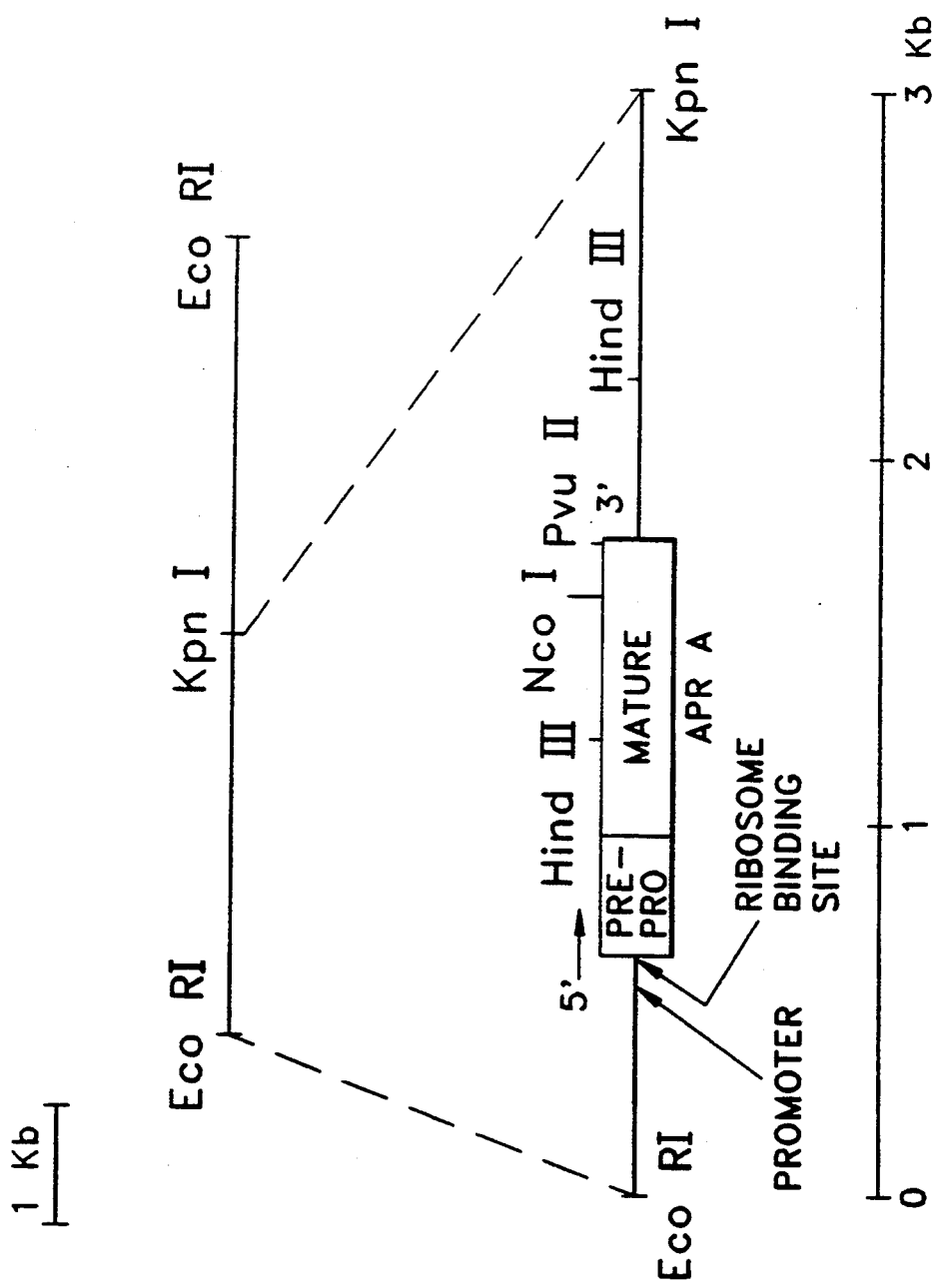
FIG. 2 is a partial restriction map of an aprA gene-containing an EcoRI-KpnI gene fragment of *Bacillus subtilis* (*B. subtilis*) strain QB127 and includes a partial restriction map of the aprA gene and flanking sequences.

It was determined that a large 6.5 kb EcoRI fragment of *B. subtilis* QB127 genomic DNA carried the aprA gene, its regulatory sequences and unrelated flanking sequences by verifying that restriction enzyme digests conformed to the results reported by Stahl, et al., supra. This was confirmed by DNA sequencing using the dideoxy chain termination method described by Sanger, et al., *J. Mol. Biol.*, 143, 161-178 (1980). A 3.0 kb EcoRI to KpnI subfragment of the 6.5 kb EcoRI fragment, as illustrated in FIG. 2, was also found to contain the aprA gene, its regulatory sequences, and unrelated flanking sequences. Although the KpnI-EcoRI fragment is reported to be 2.5 kb in length by Stahl, et al., and in the legend to FIG. 1 therein, comparison of the scale of FIG. 1 and the scaled depiction of the fragment therein reveal that, even in Stahl, et al., the KpnI-EcoRI fragment is substantially larger than 2.5 kb.

A cloning vector for Bacillus host systems, plasmid pAMB11, was constructed as follows. The plasmid pTG402 (Northern Regional Research Laboratories, United States Department of Agriculture, Peoria, Ill., strain number NRRL B-15264) was partially digested with the RsaI restriction endonuclease. Fragments were ligated to M13 mp18 (available from Bethesda Research Laboratories, Gaithersburg, Md. as catalog number 8227SA) which had been previously digested with HincII. Ligation products were introduced into *E. coli* JM103 (available from Pharmacia, Inc., Piscataway, N.J. as catalog number 27-1545-01) by transformation in accordance with the procedure of Mandel, et al., *J. Mol. Biol.*, 53, 154, (1970). Bacteriophage plaques were sprayed with 0.5M catechol (prepared in distilled water) to detect the functional expression of an xylE gene derived from pTG402. The xylE gene encodes catechol 2,3-dioxygenase and is useful for detecting promoters in a variety of organisms [Zukowski, et al., *Proc. Natl. Acad. Sci. (USA)*, 80, 1101-1105 (1983)].

The xylE gene was then transferred as a 1.0 kb EcoRI to PstI fragment to the *E. coli/B. subtilis* plasmid pHV33 (available from the American Type Culture Collection as A.T.C.C. 39217) [Primrose, et al. *Plasmid*, 6, 193-201 (1981)] obtained from R. Dedonder (Institut Pasteur, Paris, France). The pHV33 plasmid had been previously digested with EcoRI and PstI so that the xylE-containing fragment, when ligated in this region, would inactivate a gene for ampicillin resistance. The resulting plasmid, pAMB21, contains a functional xylE gene in *E. coli* host cells, but requires the addition of a promoter for xylE to be expressed in *B. subtilis* host cells. *E. coli* cells harboring pAMB21 are resistant to tetracycline (15 µg/ml) and chloramphenicol (20 µg/ml) while *B. subtilis* cells harboring pAMB21 are resistant only to chloramphenicol (5 µg/ml).

The $t_{oop}$ transcription termination sequence of bacteriophage lambda was transferred from plasmid pCFM936 (on a 400 base pair PstI to BglII fragment) to the unique PstI site of pAMB21. A synthetic nucleotide with the sequence, 5' GATCTGCA 3', was constructed to join the BglII extremity of the $t_{oop}$ fragment to the PstI site of the vector pAMB21. The resulting plasmid was designated pAMB22 and had properties identical to pAMB21 except for the inclusion of a transcription terminator. The pAMB22 plasmid is useful for detecting strong promoters that are functional in *B. subtilis*.

Figure 3:
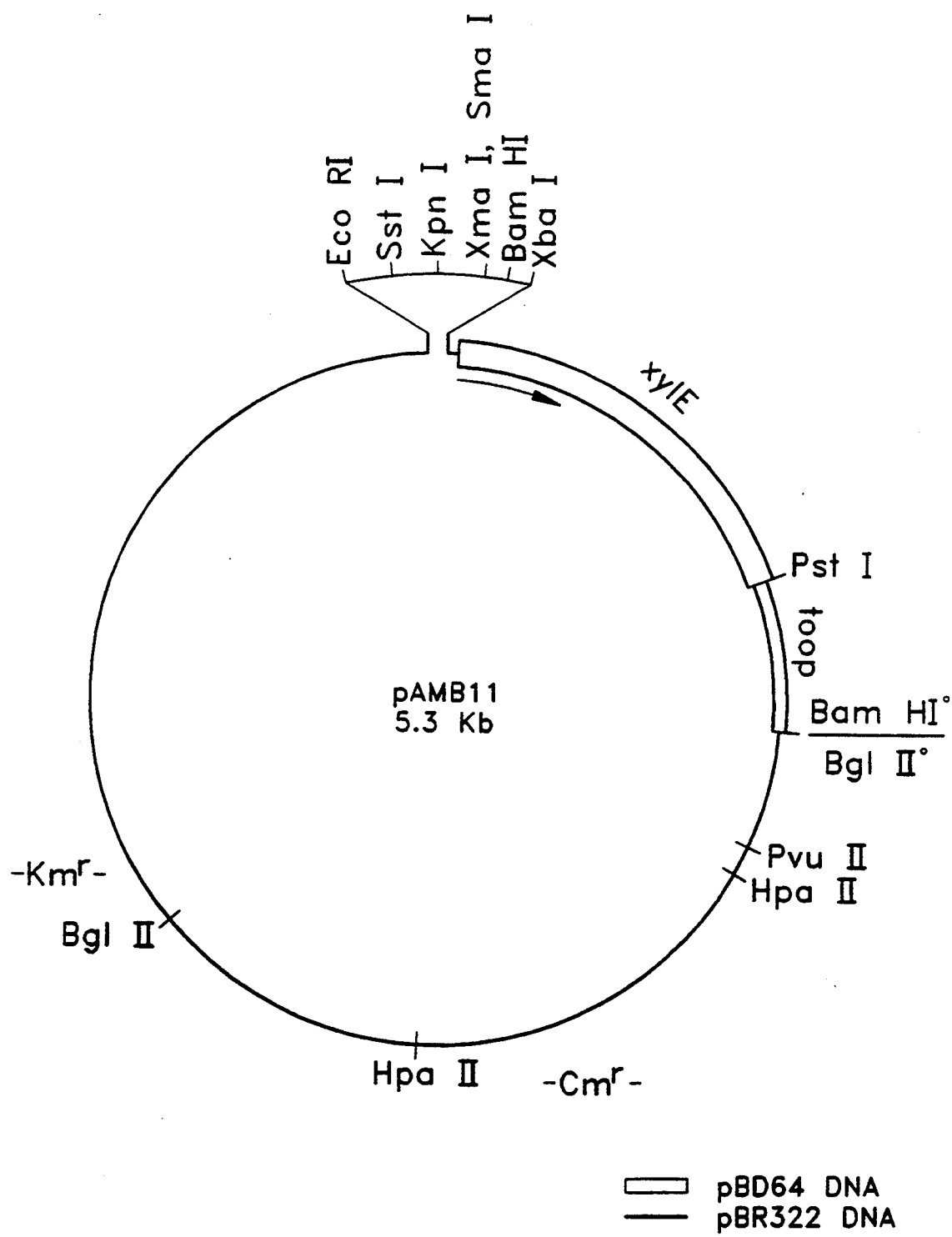
FIG. 3 is a partial restriction map of a plasmid pAMB11.

The 1.4 kb EcoRI to BglII fragment of DNA from pAMB22 that contains xylE and $t_{oop}$ was isolated from a low-melting point agarose gel after electrophoresis of restricted fragments. The 1.4 kb piece of DNA was ligated to plasmid pBD64 (available from Bacillus Genetic Stock Center, number 1E22) which had been previously digested with EcoRI and BamHI. The resulting 5.3 kb plasmid, pAMB11, contains the polylinked sequence of M13mp18 (EcoRI, SstI, XmaI, Sma, BamHI and XbaI) upstream of the xylE gene which is followed by $t_{oop}$, as shown in FIG. 3. The pAMB11plasmid is capable of replicating in *B. subtilis* and confers upon host cells resistance to chloramphenicol (5 µg/ml) and/or kanamycin (5 µg/ml).

Figure 4:
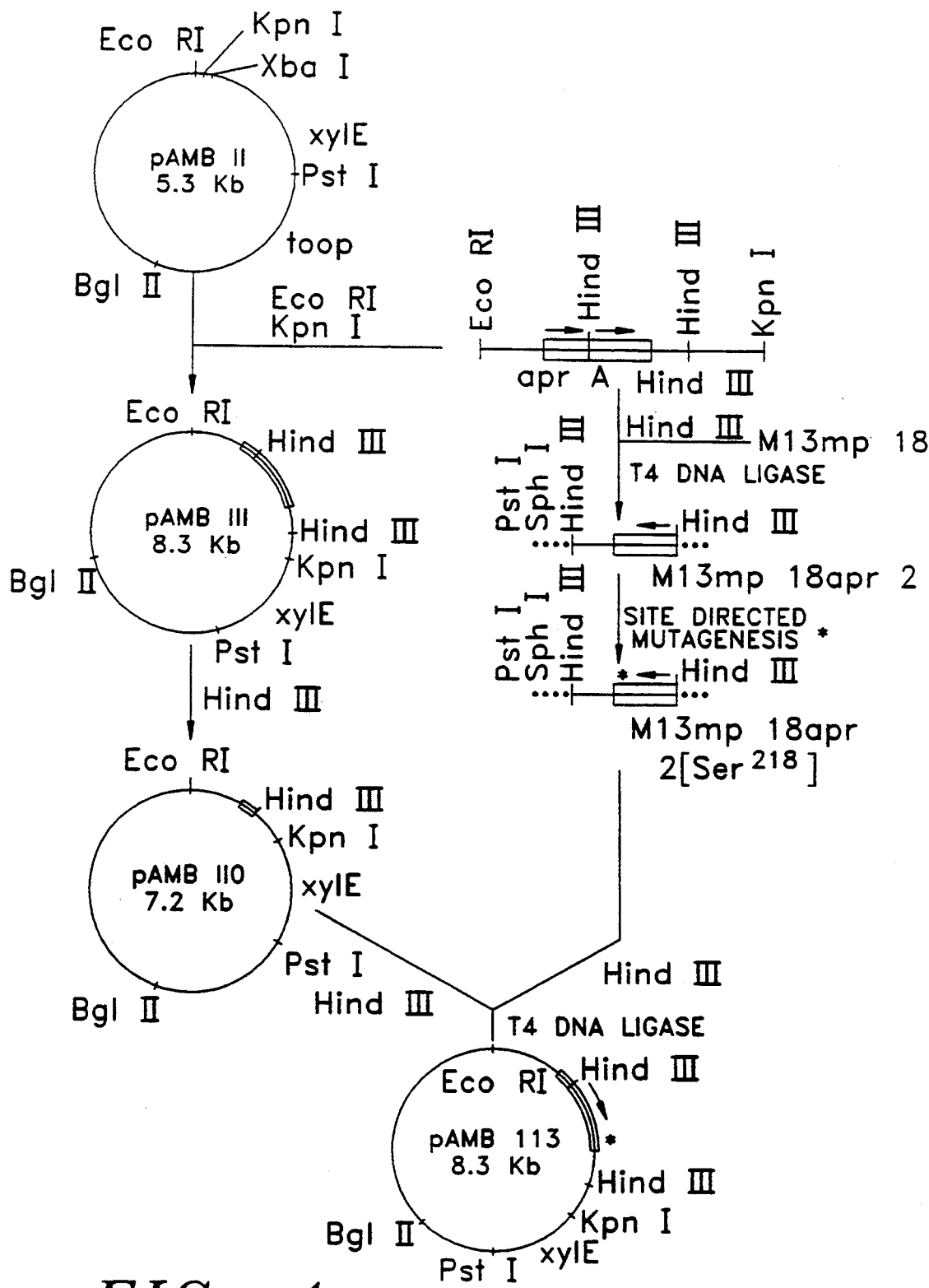
FIG. 4 is a flowchart illustrating stages in construction of pAMB113, a plasmid which directs synthesis of [Ser]$^{218}$-subtilisin from *B. subtilis* host cells.

As illustrated in FIG. 4, the purified EcoRI to KpnI fragment containing aprA was cloned onto pAMB11 to form pAMB111. Ligation products were introduced into *B. subtilis* MI112 (arg-15 leuB thr5 recE4) (available from Bacillus Genetic Stock Center as No. 1A423) by the protoplast transformation method described by Chang, et al., *Mol. Gen. Genet.*, 168, 111-115 (1979). *B. subtilis* MI112 without plasmid DNA is protease-proficient (Prt+ phenotype), but secreted levels of subtilisin are rather low. Chloramphenicol-resistant (Cm$^r$) transformants were transferred onto L-agar plates supplemented with 1.5% (w/v) skim milk and 5 µg/ml chloramphenicol, then incubated at 37° C.

After incubation at 37° C. for approximately sixteen hours, colonies of MI112 harboring plasmid pAMB111 produced a clear halo surrounding each colony. Halos were formed by the proteolytic action of subtilisin on the casein component of the skim milk medium supplement. MI112 harboring the pAMB11 vector alone had no visible halo after 16 hrs. of incubation, although a slight halo eventually developed after 40 hrs. of incubation at 37° C. Cells carrying pAMB111 were clearly distinguished from cells carrying pAMB11 by a difference in halo size. The cloning of the aprA gene in a fully functional form thus led to a high level production and secretion of subtilisin by *B. subtilis*.

EXAMPLE 2

As illustrated in FIG. 4, a 3.0 kb EcoRI to KpnI genomic fragment, the isolation of which is described in Example 1, was digested with HindIII to produce three fragments: (1) a 1.1 kb EcoRI to HindIII fragment carrying genetic regulatory sequences for aprA gene expression, the "pre-pro" region of the gene required to extracellular export of subtilisin, and the DNA sequence coding for the first 49 amino acids of mature subtilisin; (2) a 1.1 kb HindIII to HindIII fragment carrying DNA sequences coding for amino acids 50 through 275 (carboxyl-terminus) of subtilisin along with a transcription termination sequence and 3' non-coding sequences; and (3) a 0.8 kb HindIII to KpnI fragment containing 3' non-coding sequences.

The 1.1 kb fragment flanked by HindIII sites was cloned to the single HindIII site of bacteriophage M13 mp18 for the purposes of DNA sequencing and site-directed mutagenesis. One of the recombinants, designated M13 mp18 apr2, provided single stranded template DNA required for site-directed mutagenesis of the aprA gene.

The coding region of the aprA gene was sequenced and the results of the sequence are set forth in Table 1 herein. It should be noted that the specific identity of the initial 5 codons of the leader region is attributable to the report of Stahl, et al., supra, and Wong, et al., supra, of sequence information for the aprA gene, and that there exist codon sequence differences from Stahl, et al., supra, at amino acid positions 84 and 85. Specifically, Stahl, et al., supra, reports a codon GTT (coding for valine) at amino acid position 84 while the codon GTA (also coding for valine) appears in Table 1. Stahl, et al., supra, also reports a codon AGC (coding for serine) at amino acid position 85 as opposed to the codon GCG (coding for alanine) in Table 1.

TABLE 1

```
        -105
        Met  Arg  Ser  Lys  Lys  Leu  Trp  Ile  Ser  Leu  Leu  Phe  Ala
        GTG  AGA  AGC  AAA  AAA  TTG  TGG  ATC  AGC  TTG  TTG  TTT  GCG

Leu  Thr  Leu  Ile  Phe  Thr  Met  Ala  Phe  Ser  Asn  Met  Ser  Ala
TTA  ACG  TTA  ATC  TTT  ACG  ATG  GCG  TTC  AGC  AAC  ATG  TCT  GCG

Gln  Ala  Ala  Gly  Lys  Ser  Ser  Thr  Glu  Lys  Lys  Tyr  Ile  Val
CAG  GCT  GCC  GGA  AAA  AGC  AGT  ACA  GAA  AAG  AAA  TAC  ATT  GTC

Gly  Phe  Lys  Gln  Thr  Met  Ser  Ala  Met  Ser  Ser  Ala  Lys  Lys
GGA  TTT  AAA  CAG  ACA  ATG  AGT  GCC  ATG  AGT  TCC  GCC  AAG  AAA

Lys  Asp  Val  Ile  Ser  Glu  Lys  Gly  Gly  Lys  Val  Gln  Lys  Gln
AAG  GAT  GTT  ATT  TCT  GAA  AAA  GGC  GGA  AAG  GTT  CAA  AAG  CAA

Phe  Lys  Tyr  Val  Asn  Ala  Ala  Ala  Ala  Thr  Leu  Asp  Glu  Lys
TTT  AAG  TAT  GTT  AAC  GCG  GCC  GCA  GCA  ACA  TTG  GAT  GAA  AAA

Ala  Val  Lys  Glu  Leu  Lys  Lys  Asp  Pro  Ser  Val  Ala  Tyr  Val
GCT  GTA  AAA  GAA  TTG  AAA  AAA  GAT  CCG  AGC  GTT  GCA  TAT  GTG

-1   +1
Glu  Glu  Asp  His  Ile  Ala  His  Glu  Tyr  Ala  Gln  Ser  Val  Pro
GAA  GAA  GAT  CAT  ATT  GCA  CAT  GAA  TAT  GCG  CAA  TCT  GTT  CCT

10
Tyr  Gly  Ile  Ser  Gln  Ile  Lys  Ala  Pro  Ala  Leu  His  Ser  Gln
TAT  GGC  ATT  TCT  CAA  ATT  AAA  GCG  CCG  GCT  CTT  CAC  TCT  CAA 20                                                          30
Gly  Tyr  Thr  Gly  Ser  Asn  Val  Lys  Val  Ala  Val  Ile  Asp  Ser
GGC  TAC  ACA  GGC  TCT  AAC  GTA  AAA  GTA  GCT  GTT  ATC  GAC  AGC

40
Gly  Ile  Asp  Ser  Ser  His  Pro  Asp  Leu  Asn  Val  Arg  Gly  Gly
GGA  ATT  GAC  TCT  TCT  CAT  CCT  GAC  TTA  AAC  GTC  AGA  GGC  GGA 50                                                           60
Ala  Ser  Phe  Val  Pro  Ser  Glu  Thr  Asn  Pro  Tyr  Gln  Asp  Gly
GCA  AGC  TTC  GTA  CCT  TCT  GAA  ACA  AAC  CCA  TAC  CAG  GAC  GGC

70
Ser  Ser  His  Gly  Thr  His  Val  Ala  Gly  Thr  Ile  Ala  Ala  Leu
AGT  TCT  CAC  GGT  ACG  CAT  GTA  GCC  GGT  ACG  ATT  GCC  GCT  CTT

80
Asn  Asn  Ser  Ile  Gly  Val  Leu  Gly  Val  Ala  Pro  Ser  Ala  Ser
AAT  AAC  TCA  ATC  GGT  GTT  CTG  GGC  GTA  GCG  CCA  AGC  GCA  TCA 90                                             100
Leu  Tyr  Ala  Val  Lys  Val  Leu  Asp  Ser  Thr  Gly  Ser  Gly  Gln
TTA  TAT  GCA  GTA  AAA  GTG  CTT  GAT  TCA  ACA  GGA  AGC  GGC  CAA

110
Tyr  Ser  Trp  Ile  Ile  Asn  Gly  Ile  Glu  Trp  Ala  Ile  Ser  Asn
TAT  AGC  TGG  ATT  ATT  AAC  GGC  ATT  GAG  TGG  GCC  ATT  TCC  AAC 120                                                    130
Asn  Met  Asp  Val  Ile  Asn  Met  Ser  Leu  Gly  Gly  Pro  Thr  Gly
AAT  ATG  GAT  GTT  ATC  AAC  ATG  AGC  CTT  GGC  GGA  CCT  ACT  GGT

140
Ser  Thr  Ala  Leu  Lys  Thr  Val  Val  Asp  Lys  Ala  Val  Ser  Ser
TCT  ACA  GCG  CTG  AAA  ACA  GTC  GTT  GAC  AAA  GCC  GTT  TCC  AGC

150
Gly  Ile  Val  Val  Ala  Ala  Ala  Ala  Gly  Asn  Glu  Gly  Ser  Ser
GGT  ATC  GTC  GTT  GCT  GCC  GCA  GCC  GGA  AAC  GAA  GGT  TCA  TCC 160                                            170
Gly  Ser  Thr  Ser  Thr  Val  Gly  Tyr  Pro  Ala  Lys  Tyr  Pro  Ser
GGA  AGC  ACA  AGC  ACA  GTC  GGC  TAC  CCT  GCA  AAA  TAT  CCT  TCT

180
Thr  Ile  Ala  Val  Gly  Ala  Val  Asn  Ser  Ser  Asn  Gln  Arg  Ala
ACT  ATT  GCA  GTA  GGT  GCG  GTA  AAC  AGC  AGC  AAC  CAA  AGA  GCT
```

TABLE 1-continued

```
              190                                            200
Ser   Phe   Ser   Ser   Ala   Gly   Ser   Glu   Leu   Asp   Val   Met   Ala   Pro
TCA   TTC   TCC   AGC   GCA   GGT   TCT   GAG   CTT   GAT   GTG   ATG   GCT   CCT

210
Gly   Val   Ser   Ile   Gln   Ser   Thr   Leu   Pro   Gly   Gly   Thr   Tyr   Gly
GGC   GTG   TCC   ATC   CAA   AGC   ACA   CTT   CCT   GGA   GGC   ACT   TAC   GGC

220
Ala   Tyr   Asn   Gly   Thr   Ser   Met   Ala   Thr   Pro   His   Val   Ala   Gly
GCT   TAT   AAC   GGA   ACG   TCC   ATG   GCG   ACT   CCT   CAC   GTT   GCC   GGA 230                                       240
Ala   Ala   Ala   Leu   Ile   Leu   Ser   Lys   His   Pro   Thr   Trp   Thr   Asn
GCA   GCA   GCG   TTA   ATT   CTT   TCT   AAG   CAC   CCG   ACT   TGG   ACA   AAC

250
Ala   Gln   Val   Arg   Asp   Arg   Leu   Glu   Ser   Thr   Ala   Thr   Tyr   Leu
GCG   CAA   GTC   CGT   GAT   CGT   TTA   GAA   AGC   ACT   GCA   ACA   TAT   CTT 260                                                       270
Gly   Asn   Ser   Phe   Tyr   Tyr   Gly   Lys   Gly   Leu   Ile   Asn   Val   Gln
GGA   AAC   TCT   TTC   TAC   TAT   GGA   AAA   GGG   TTA   ATC   AAC   GTA   CAA

275
Ala   Ala   Ala   Gln   OC
GCA   GCT   GCA   CAA   TAA   TAGTAAAAAGAAGCAGGTTCCTCCATACCTGCT

TCTTTTTATTTGTCAGCATCCTGATGTTCCGGCGCATTCTC
```

Bacteriophage M13 mp18 apr2 was constructed by inserting a 1.1 kb HindIII to HindIII fragment of *B. subtilis* QB127 genomic DNA, carrying nucleotide sequences coding for amino acids 50 through 275 (carboxyl-terminus) of aprA-subtilisin along with a transcription termination sequence and 3' non-coding sequences, in the unique HindIII site of bacteriophage M13 mp18. To eliminate the 3' non-coding sequences, a KpnI restriction endonuclease site was introduced, by site-directed mutagenesis, at a position immediately following the transcription termination sequence.

Site-directed mutagenesis was conducted in accordance with a procedure described by Norrander et. al., *Gene*, 26, 101–106 (1983). Single-stranded DNA from M13 mp18 apr2 was annealed to a primer, $$\text{5' TCCTGA}\underline{\text{GGTACC}}\text{GGCGCATTC 3'}$$
       *          * which was synthesized by the phosphite method described by Beaucage et. al., *Tetrahedron Letters* 22, 1859–1862 (1981). The primer was homologous to the nucleotides in this region except for two (marked by asterisks), where a thymine (T) was changed to guanine (G) and another thymine (T) was changed to adenine (A), thus creating a KpnI site (underlined) in this region.

The primer was annealed to M13 mp18 apr2 DNA at 65° C. and the annealed DNA was slowly cooled to approximately 22° C. and then polymerized for 2 hr. at 15° C. in a reaction mixture which consisted of 12.5 μl of annealed DNA solution, 2.5 μl of 10 mM each of dATP, dCTP and dGTP, 20 μl of 12 mMATP, 0.1 μl Klenow DNA polymerase, 0.1 μl T4 DNA ligase and 13 μl sterile distilled water. The resulting double-stranded, covalently closed circular DNA was introduced into *E. coli* JM103 by transfection.

Bacteriophage plaques were then transferred to Gene Screen TM (New England Nuclear, Beverly, Mass.) hybridization membranes. Plaques which contained DNA with the desired base changes were identified by hybridization to the radioactively labeled ($\gamma$-$^{32}$P) synthetic oligonucleotide used for the mutagenic priming reaction described above. Hybridization was performed at a restrictive temperature (65° C.) in order that only DNA carrying a KpnI mutation would hybridize to the synthetic oligonucleotide. The presence of the KpnI mutation downstream of the aprA gene on DNA from a single purified plaque, designated M13 mp18 apr2 KpnI, was confirmed by DNA sequencing by the procedure described by Sanger et. al., supra and restriction enzyme analysis.

Figure 7:
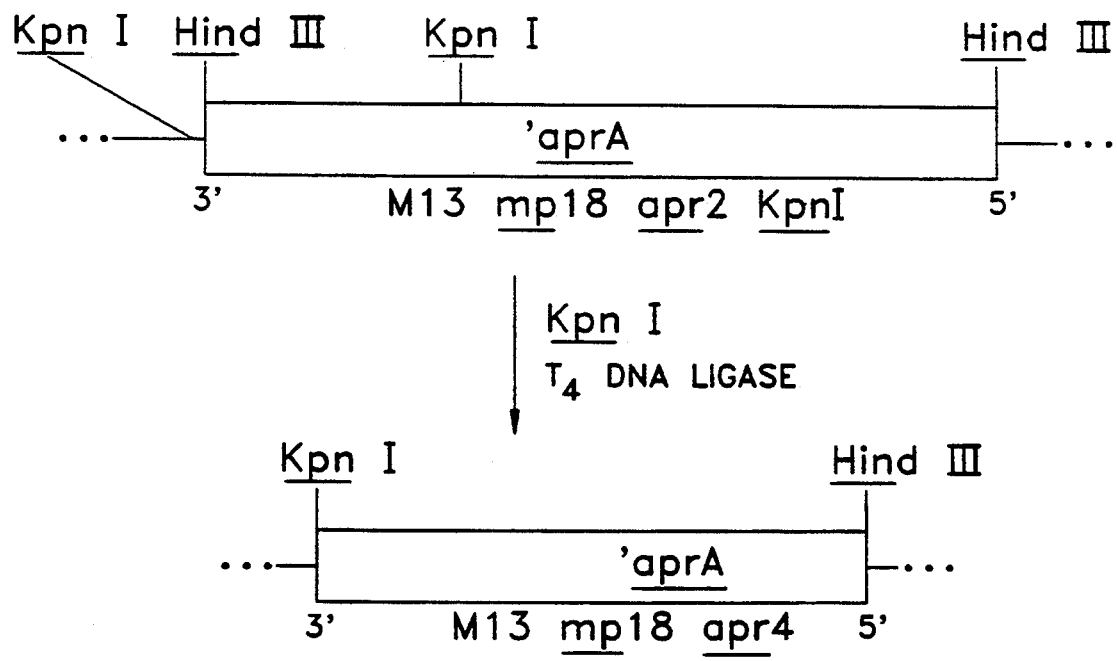
FIG. 7 illustrates the construction of M13 mp19 aprA143.

A 1.1 kb segment carrying most of the 3' non-coding region was deleted by digesting M13 mp18 apr2 KpnI with KpnI, religating digestion products at a concentration of 500 ng DNA/ml, then introducing the ligation products into *E. coli* JM103 by transfection. Bacteriophage plaques which contained DNA with the desired 0.35 kb deletion were identified by restriction endonuclease analysis. Bacteriophage from one such plaque was designated M13 mp18 apr4 (FIG. 7). M13 mp18 apr4 provided single-stranded template DNA for site-directed mutagenesis of the aprA gene described hereinafter.

EXAMPLE 3

In order to express mutated subtilisin genes in *B. subtilis*, the plasmid pAMB106 was constructed as a vehicle for the mutated gene, as follows:

1) pAMB111 was digested with HindIII. A 1.1 kb segment carrying most of the aprA gene was deleted by re-ligating HindIII digestion products of pAMB111 at a concentration of approximately 1 μg/ml. This resulted in the formation of pAMB110 as illustrated in FIG. 4. The pAMB110 plasmid carries genetic regulatory sequences for expression of the subtilisin gene, the "pre-pro" region required for secretion of subtilisin, and the DNA sequence coding for the 3' non-coding region of mature subtilisin and the first 49 amino acids of mature subtilisin.

2) Plasmid pAMB110 was digested with BamHI and PstI in combination. This produced DNA fragments of two sizes, 6.2 kb and 1.0 kb. The 1.0 kb fragment carries the xylE gene, coding for catechol 2,3-dioxygenase, from the TOL plasmid of *Pseudomonas putida* mt-2 (Zukowski et. al., supra).

3) The larger, 6.2 kb BamHI-PstI fragment was self-ligated with the aid of a single-stranded synthetic oligonucleotide, 5' GATCTGCA 3' which was synthesized by the phosphite method described by Beaucage et. al., supra, and T4 DNA ligase. Ligation products were introduced into *B. subtilis* MI112 (arg-15 leuB thr5 recE4 (available from Bacillus Genetic Stock Center as No. 1A423) by the protoplast transformation method described by Change et. al., Mol. Gen. Genet. 168, 111–115 (1979).

Figure 6:
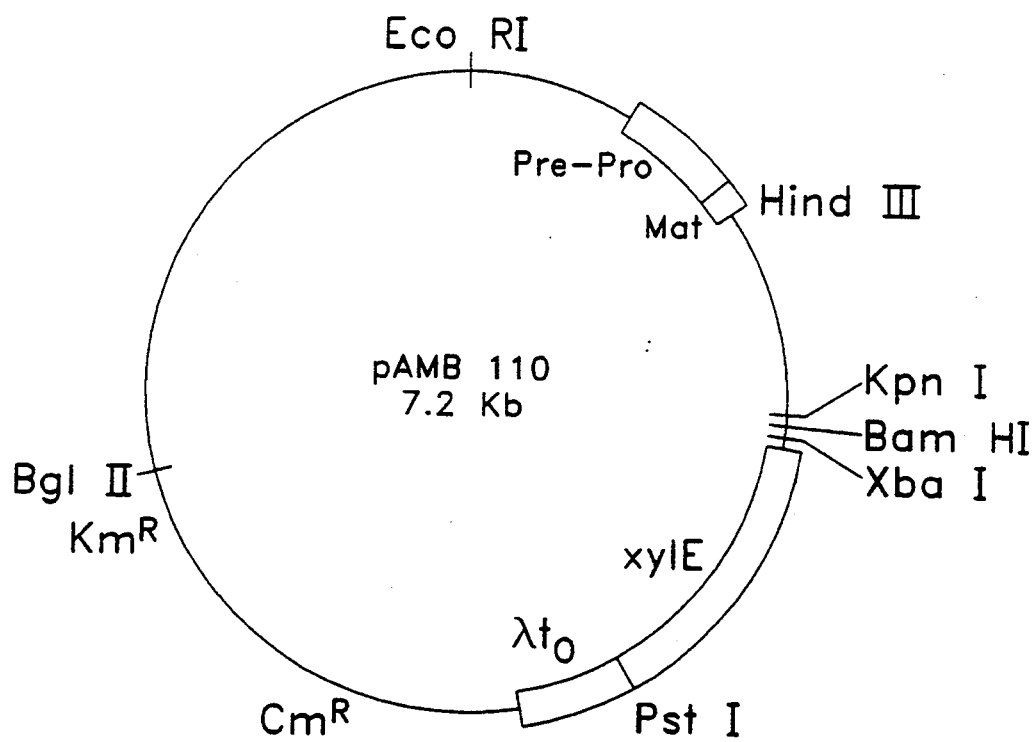
FIG. 6 illustrates the construction of pAMB106.
Figure 6:
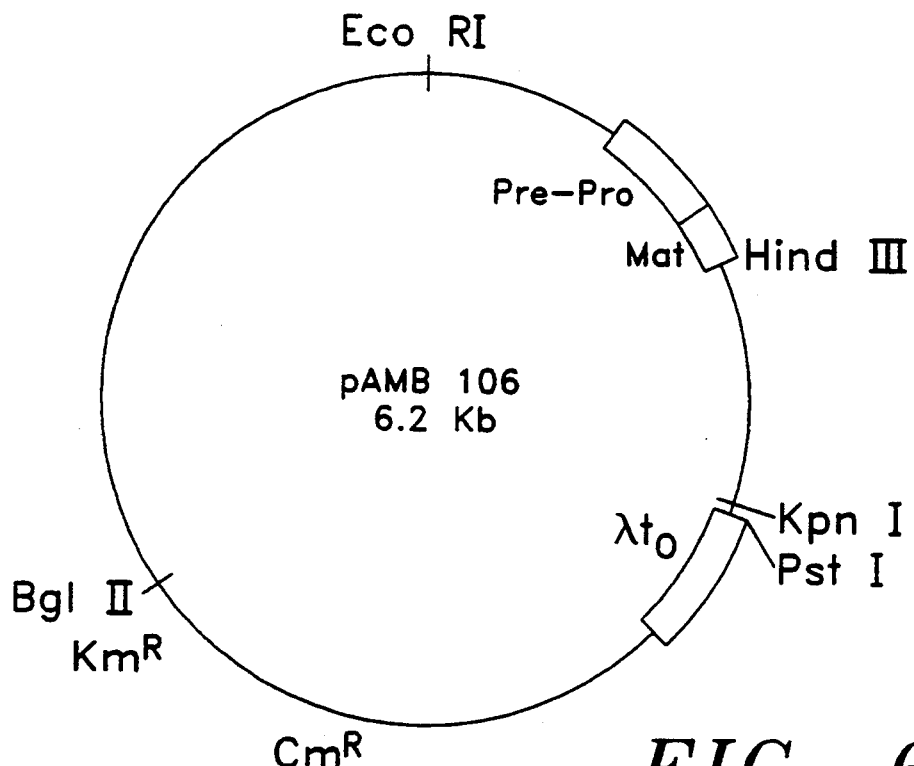

Chloramphenicol-resistant (Cm$^R$) colonies were screened for plasmid content. The 6.2 kb plasmid pAMB106 was identified by restriction endonuclease analysis. It is identical to plasmid pAMB110 except that xylE has been deleted (FIG. 6).

Because it is lacking DNA coding for amino acids 50 through 275 of aprA subtilisin, pAMB106 does not synthesize subtilisin when introduced into *B. subtilis* host cells. Subtilisin is synthesized only after insertion of the remainder of the subtilisin gene, i.e., either the native DNA sequence or an analog-encoding sequence.

EXAMPLE 4

Preparation of a [Serine$^{109}$] Subtilisin Analog

Single-stranded DNA from bacteriophage M13mp18 apr4 was annealed to a primer,

```
            *
5' TGG ATT ATT AGC GGC ATT GAG TGG 3'
   106 107 108 109 110 111 112 113
   TRP ILE ILE SER GLY ILE GLU TRP
``` which was synthesized by the phosphite method described by Beaucage et. al., supra. The primer was homologous to the nucleotides comprising codons for amino acids 106 through 113 of aprA-subtilisin except for one base change (marked by an asterisk) where an A was changed to a G to allow for the transition which would change Asn$^{109}$ (codon AAC) to Set$^{109}$ (codon AGC).

The primer was annealed to M13mp18 apr4 DNA at 65° C. and the annealed DNA was slowly cooled to approximately 22° C. and then polymerized, ligated and transfected as described in Example 2.

Bacteriophage plaques were transferred to hybridization membranes, then those which contained DNA with the desired base change were identified by hybridization to a radioactively labeled (α-$^{32}$P) oligonucleotide used for the mutagenic priming reaction described above. Hybridization was performed at 65° C. One positive plaque contained bacteriophage designated as M13mp18 apr4[Ser$^{109}$]. Double-stranded DNA from this bacteriophage was digested with HindIII and KpnI in combination, then the 750 bp fragment carrying the mutated portion of the aprA-subtilisin gene was ligated to pAMB106 which had been previously digested with HindIII and KpnI. The resulting plasmid, pAMB129, may be introduced into a suitable *B. subtilis* host cells for synthesis and secretion of [Ser$^{109}$]-subtilisin.

EXAMPLE 5

Preparation of a [Serine$^{109}$, Serine$^{218}$] Subtilisin Analog

Single-stranded DNA from M13mp18 apr4[Ser$^{109}$] was annealed to a primer:

```
             *
5' GGC GCT TAT AGC GGA AC 3'
   215 216 217 218 219 220
   GLY ALA TYR SER GLY THR
``` which was synthesized by the phosphite method described by Beuacage et. al., supra. The primer was homologous to nucleotides comprising codons for amino acids 215 through 220 of aprA-subtilisin except for one base change (marked by an asterisk) where an A was changed to a G to allow for the transition which would change Asn$^{218}$ (codon AAC) to Ser$^{218}$ (codon AGC). The conditions for annealing, polymerization, ligation, transfection, and identification of positive plaques were as described in Example 2. A single purified plaque contained bacteriophage designed as M13mp18 apr4 [Ser$^{109}$, Ser$^{218}$]. Double-stranded DNA from this bacteriophage was digested with HindIII and KpnI in combination, then a 750 bp fragment carrying the two mutations was ligated to pAMB106 which had been previously digested with HindIII and KpnI. The resulting plasmid, pAMB130, may be introduced into *B. subtilis* host cells for synthesis and secretion of [Ser$^{109}$, Ser$^{218}$]-subtilisin

EXAMPLE 6

Preparation of a [Asp$^{76}$, Ser$^{109}$, Ser$^{218}$] Subtilisin Analog

Single-stranded DNA from M13mp18 apr4 [Ser$^{109}$, Ser$^{218}$] was annealed to a primer:

```
            *
5' GCT CTT GAT AAC TCA ATC 3'
   74  75  76  77  78  79
   ALA LEU ASP ASN SER ILE
``` which was synthesized by the phosphite method described by Beaucage et. al., supra. The primer was homologous to the nucleotides comprising codons for amino acids 74 through 79 of aprA-subtilisin except for one base change (marked by an asterisk), where an A was changed to a G to allow for the transition which would change Asn$^{76}$ (codon AAT) to Asp$^{76}$ (codon GAT).

The primer was annealed to M13mp18 [Ser$^{109}$, Ser$^{218}$] DNA at 65° C. and the annealed DNA was slowly cooled to approximately 22° C. and polymerized, ligated and transfected as described in Example 2.

Bacteriophage plaques were transferred to hybridization membranes and those which contained DNA with the desired base change were identified by hybridization as described in Example 2 except that hybridization was performed at 46° C. One positive plaque contained bacteriophage designated at M13mp18 apr4 [Asp$^{76}$, Ser$^{109}$, Ser$^{218}$]. Double-stranded DNA from the bacteriophage was digested with HindIII and KpnI in combination, then a 750 bp fragment carrying the three mutations of the aprA-subtilisin gene was ligated to pAMB106 which had been previously digested with HindIII and KpnI. The resulting plasmid, pAMB131, may be introduced into *B. subtilis* host cells for synthesis and secretion of [Asp$^{76}$, Ser$^{109}$, Ser$^{218}$]-subtilisin.

EXAMPLE 7

Preparation of a [Asp$^{76}$, Glu$^{79}$, Ser$^{109}$, Ser$^{218}$] Subtilisin Analog Single-stranded DNA from M13mp18 apr4 [Asp$^{76}$, Ser$^{109}$, Ser$^{218}$] was annealed to a primer:

```
               *   *   *
5'  T GAT AAC TCA GAA GGT GTT CTG G  3'
    75  76  77  78  79  80  81  82 83
        ASP ASN SER GLU GLY VAL LEU
``` which was synthesized by the phosphite method described by Beaucage et al., supra. The primer was homologous to the nucleotides comprising partial codons for amino acids 75 and 83 and entire codons for amino acids 76 through 75 and 83 and entire codons for amino acids 76 through 82 of [Asp$^{76}$, Ser$^{109}$, Ser$^{218}$]-subtilisin except for three base changes (marked by asterisks), wherein an A was changed to a G, a T was changed to an A, and a C was changed to an A, which changed Ile$^{79}$ (codon ATC) to Glu$^{79}$ (codon GAA).

The primer was annealed to M13mp18 apr4 [Asp$^{76}$, Ser$^{109}$, Ser$^{218}$] DNA at 65° C. and the annealed DNA was slowly cooled to approximately 22° C. and was polymerized, ligated and transfected as described in Example 2.

Bacteriophage plaques were transferred to hybridization membranes and those which contained the desired base changes were identified by hybridization as described in Example 2 except that hybridization was performed at 45° C. One positive plaque contained bacteriophage designated as M13mp18 apr4 [Asp$^{76}$, Glu$^{79}$, Ser$^{109}$, Ser$^{218}$]. Double-stranded DNA from this bacteriophage was digested with HindIII and KpnI in combination, then a 750 bp fragment carrying the four mutations of the aprA-subtilisin gene was ligated to pAMB106 which had ben previously digested with HindIII and KpnI. The resulting plasmid, pAMB133, may be introduced into *B. subtilis* host cells for synthesis and secretion of [Asp$^{76}$, Glu$^{79}$, Ser$^{109}$, Ser$^{218}$]-subtilisin C. and was polymerized, ligated and transfected as described in Example 2.

EXAMPLE 8

Preparation of a [Asp$^{76}$, Ser$^{109}$, Ser$^{218}$, Ala222]-Subtilisin Analog Single-stranded DNA from M13 mp18 apr4 [Asp$^{76}$, Ser$^{109}$, Ser$^{218}$] was annealed to the primer:

```
            *    *
5' GGA ACG TCC GCG GCG ACT 3'
   219 220 221 222 223 224
   Gly Thr Ser Ala Ala Thr
``` which was synthesized by the phosphite method described by Beaucage et al., supra. The primer was homologous to the nucleotides comprising codons for amino acids 219 through 224 of [Asp$^{76}$, Ser$^{109}$, Ser$^{218}$]-subtilisin except for two base changes (marked by asterisks), wherein an adenine (A) was changed to a guanine (G) and a thymine (T) was changed to a cytosine (C), which changed the Met$^{222}$ (codon ATG) to Ala$^{222}$ (codon GCG). The primer was annealed to M13mp18 apr4 [Asp$^{76}$, Ser$^{109}$, Ser$^{218}$] DNA at 65° C. and the annealed DNA was slowly cooled to approximately 22°

Bacteriophage plaques were transferred to hybridization membranes and those which contained desired base changes were identified by hybridization as described in Example 2 except that hybridization was performed at 58° C. One positive plaque contained bacteriophage designated as M13 mp18 apr4 [Asp$^{76}$, Ser$^{109}$, Ser$^{218}$, Ala$^{222}$]. Double stranded DNA from this bacteriophage was digested with HindIII and KpnI in combination, then at 750 bp fragment of DNA carrying the four mutations of the aprA-subtilisin gene was ligated to pAMB106 which had been previously digested with HindIII and KpnI. The resulting plasmid, pAMB143, may be introduced and propagated in Bacillus host cells for synthesis and secretion of [Asp$^{76}$, Ser$^{109}$, Ser$^{218}$, Ala$^{222}$]-subtilisin.

EXAMPLE 9

Preparation of M13 mp19 aprA143

Plasmid pAMB143 was digested with EcoRI and KpnI in combination. A 1.8 kb fragment of DNA carrying the entire gene for [Asp$^{76}$, Ser$^{109}$, Ser$^{218}$, Ala$^{222}$]-subtilisin, along with its flanking sequences required for initiation of transcription and translation and termination of transcription and translation, was transferred to bacteriophage M13mp19 (available from Bethesda Research Laboratories, Gaithersburg, Md., as catalogue no. 8229SA) which had been digested with EcoRI and KpnI. One of the recombinant bacteriophage DNA resulting from this procedure was designated M13mp19 aprA143, and provided single-stranded template DNA required for site-directed mutagenesis of the [Asp$^{76}$, Ser$^{109}$, Ser$^{218}$, Ala$^{222}$]-subtilisin gene.

EXAMPLE 10

Preparation of a [Leu$^{31}$, Asp$^{76}$, Ser$^{109}$, Ser$^{218}$, Ala$^{222}$]-Subtilisin Analog Single-stranded DNA from M13 mp19 aprA143 was annealed to the primer:

```
            *   *
5' GTA GCT GTT TTA GAC AGC GGA 3'
   28  29  30  31  32  33  34
   Val Ala Val Leu Asp Ser Gly
``` which was synthesized by the phosphite method described by Beaucage et al., supra. The primer was homologous to the nucleotides comprising codons for amino acids 28 through 34 of [Asp$^{76}$, Ser$^{109}$, Ser$^{218}$, Ala$^{222}$]-subtilisin except for two base changes (marked by asterisks), wherein an adenine (A) was changed to thymine (T) and a cytosine (C) was changed to adenine (A), which changed the Ile$^{31}$ (codon ATC) to Leu$^{31}$ (codon TTA). The primer was annealed to M13 mp19 aprA143 DNA at 65° C. and the annealed DNA was slowly cooled to approximately 22° C. and was polymerized, ligated and transfected as described in Example 2.

Bacteriophage plaques were transferred to hybridization membranes and those which contained desired base changes were identified by hybridization as described in Example 2 except that hybridization was performed at 57° C. One positive plaque contained bacteriophage designated as M13mp19, aprA144 and carried DNA coding for [Leu$^{31}$, Asp$^{76}$, Ser$^{109}$, Ser$^{218}$, Ala$^{222}$]-subtilisin. Double-stranded DNA from this bacteriophage was digested with EcoRI and KpnI in combination, then a 1.8 kb fragment of DNA carrying the five mutations of the aprA-subtilisin gene was ligated to pAMB106 which had been previously digested with EcoRI and KpnI. The resulting plasmid, pAMB144, may be introduced and propagated in Bacillus host cells for synthesis and secretion of [Leu$^{31}$, Asp$^{76}$, Ser$^{109}$, Ser$^{218}$, Ala$^{222}$]-subtilisin.

EXAMPLE 11

Preparation of a [Asp$^{76}$, Ser$^{109}$, Leu$^{124}$, Ser$^{218}$, Ala$^{222}$]-Subtilisin Analog Single-stranded DNA from M13mp19 aprA143 was annealed to the primer:

```
                  *   *
5' AT GTT ATC AAC TTA AGC CTT GG 3'
      121 122 123 124 125 126
      Val Ile Asn Leu Ser Leu
``` which was synthesized by the phosphite method described by Beaucage et al., supra. The primer was homologous to the nucleotides comprising partial codons for amino acids 120 and 127 and complete codons for amino acids 121 through 126 of [Asp$^{76}$, Ser$^{109}$, Ser$^{218}$, Ala$^{222}$]-subtilisin except for two base changes (marked by asterisks), wherein an adenine (A) was changed to thymine (T) and a guanine (G) was changed to adenine (A), which changed the Met$^{124}$ (codon ATG) to Leu$^{124}$ (codon TTA).

The primer was annealed to M13mp19 aprA143 DNA at 65° C. and the annealed DNA was slowly cooled to approximately 22° C. and was polymerized, ligated and transfected as described in Example 2.

Bacteriophage plaques were transferred to hybridization membranes and those which contained desired base changes were identified by hybridization as described in Example 2 except that hybridization was performed at 59° C. One positive plaque contained bacteriophage designated as M13 mp19 aprA145 and carried DNA coding for [Asp$^{76}$, Ser$^{109}$, Leu$^{124}$, Ser$^{218}$, Ala$^{222}$]-subtilisin. Double-stranded DNA from this bacteriophage was digested with EcoRI and KpnI in combination, then a 1.8 kb fragment of DNA carrying the five mutations of the aprA-subtilisin gene was ligated to pAMB106 which had been previously digested with EcoRI and KpnI. The resulting plasmid, pAMB145, may be introduced and propagated in Bacillus host cells for synthesis and secretion of [Asp$^{76}$, Ser$^{109}$, Leu$^{124}$, Ser$^{218}$, Ala$^{222}$]-subtilisin.

EXAMPLE 12

Figure 5:
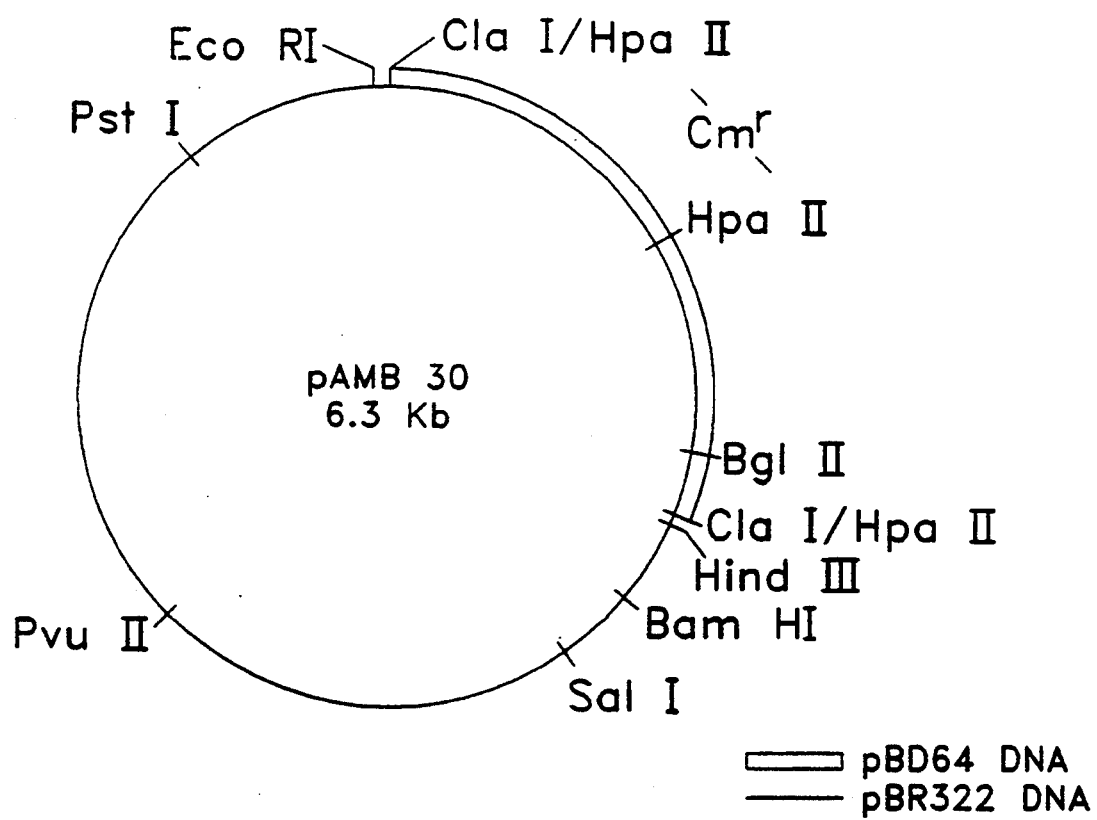
FIG. 5 is a partial restriction map of pAMB30 plasmid.

Because most Bacilli secrete alkaline and/or neutral proteases into the surrounding growth medium, it is preferable that mutations be introduced into endogenous alkaline and neutral protease genes of B. subtilis to block their synthesis so that mutated subtilisin genes, when introduced into the mutant cell, may produce mutated subtilisins which will then be secreted in a medium free of other proteases likely to interfere with isolation of intact subtilisin analogs. Two mutant B. subtilis strains BZ24 and BZ25, which produce no detectable extracellular proteases, were constructed in accordance with the following procedure:

First, a plasmid vehicle capable of replicating in E. coli, but not in B. subtilis unless integrated into the B. subtilis chromosome by homologous recombination, was constructed as follows. Plasmid pBD64 (Bacillus Genetic Stock Center, Number 1E22) was digested to completion with HpaII to produce three fragments of 2.95 kb, 1.0 kb and 0.75 kb in size. These fragments were then ligated as a mixture to plasmid pBR322 (A.T.C.C. 37017) which previously had been digested with ClaI. The ligation products were introduced into E. coli C600 (available from the American Type Culture Collection as A.T.C.C. 23724) by transformation [Mandel, et al., J. Mol. Biol., 53, 154 (1970)]. Selection was for cells resistant to chloramphenicol (20 μg/ml) and ampicillin (50 μg/ml). Plasmid DNA from 12 transformants was prepared by an alkaline extraction procedure described by Birnboim, et al., Nucleic Acids Res., 7, 1513–1523 (1979), then digested with HindIII and EcoRI in combination to verify the presence of inserted fragment(s). One such plasmid, designated pAMB30, was found to carry the 1.0 and 0.75 kb HpaII fragments of pBD64 in the ClaI site of pBR322. These fragments contain the chloramphenicol acetyltransferase (cat) gene which is functional in E. coli and B. subtilis. Digestions with BglII and, separately, with Sau3A confirmed the identity and orientation of the cat gene on pAMB30, as illustrated in FIG. 5.

Because pAMB30 lacks an origin of replication sequence which is functional in B. subtilis, it cannot replicate as an autonomous replicon in B. subtilis host cells. On the other hand, pAMB30 contains the pBR322-derived origin of replication which is functional in E. coli, thus the plasmid can be propagated in E. coli host cells. Plasmid pAMB30 is useful in at least 2 ways. First, a fragment of DNA which contains a functional origin of replication in B. subtilis may be detected when cloned onto pAMB30 such that the plasmid will autonomously replicate in the extrachromosomal state. Second, plasmid pAMB30 can integrate into the genome of B. subtilis at a site of homology between the chromosome and B. subtilis DNA cloned onto pAMB30. This has been demonstrated by Haldenwang, et al., J. Bacteriol., 142, 90–98 (1980) and Young, J. Gen. Microbiol., 129, 1497–1512 (1983) using plasmid vehicles similar to, but not identical to pAMB30.

Plasmid pAMB21 (described in Example 1) was digested with EcoRI and PstI to isolate the xylE gene on a 1.0 kb fragment. The fragment was ligated to pAMB30 which had been previously digested with EcoRI and PstI. Ligation products were introduced into E. coli C600 by transformation. Selection was for chloramphenicol resistant (20 μg/ml) host cells which were sensitive to ampicillin (50 μg/ml) due to the insertion of the xylE fragment of pAMB21 into the structural gene for ampicillin resistance of pAMB30. The resulting plasmid, pAMB30/21, has properties identical to pAMB30 but has, in addition, a functional xylE gene.

Plasmid pAMB110, which carries the aprA gene deleted of a region coding for the latter 226 amino acids of mature subtilisin, was digested with EcoRI and KpnI. The 1.9 kb fragment of B. subtilis DNA containing genetic regulatory sequences for aprA gene expression, "the pre-pro" region, the DNA sequence coding for the first 49 amino acids of mature subtilisin and 3' non-coding sequences was ligated to pAMB30/21 that had been previously digested with EcoRI and KpnI. Ligation products were introduced into E. coli C600 by transformation. Plasmid DNA from several transformants was isolated by the alkaline extraction procedure of Birnboim, et al., supra, and the presence of the inserted 1.9 kb fragment was verified by multiple restriction endonuclease digestions. One such plasmid, designated pAMB301, was retained for further use.

B. subtilis strain BGSC1A274 (Bacillus Genetic Stock Center) carries a mutation at the npr locus and is incapable of producing extracellular neutral protease. The plasmid pAMB301 was integrated into the genome of B. subtilis BGSC1A274 by transformation of competent cells [Spizizen, Proc. Natl. Acad. Sci. (USA), 44, 1072–1078 (1958)]. Selection was for chloramphenicol-resistant (5 μg/ml) host cells which were then transferred by sterile toothpicks to L-agar supplemented with 1.5% (w/v) powdered skim milk and (5 μg/ml) cloramphenicol. Those cells which failed to produce a clear halo surrounding the colony were deficient in the ability to produce extracellular neutral and serine proteases due to the combination of the npr mutation along with the newly introduced aprA mutation. The aprA mutation was a deletion of the latter 226 amino acids of mature subtilisin due to the replacement of the wild-type aprA gene with the deleted version carried on pAMB301. One such strain, designated BZ24, has the Npr$^-$ Apr$^-$ Cm$^r$ phenotype, thus it produces no detectable extracellular neutral protease nor extracellular alkaline protease and is resistant to chloramphenicol at 5 μg/ml. Southern blotting [Southern, J. Mol. Biol., 98, 503–517 (1975)] was used to confirm the deletion in the aprA gene on the chromosome of B. subtilis BZ24. Cultivation of B. subtilis BZ24 in Antibiotic Medium No. 3 (Penassay Broth, Difco, Detroit, Mich.) in the absence of antibiotic selection for approximately 32 generations led to the isolation of a derivative strain of BZ24 in which the cat gene conferring chloramphenicol resistance upon host cells was lost due to its instability in the BZ24 chromosome. Such a phenomenon has been previously observed by Stahl, et al., J. Bacteriol., 158, 411–418 (1984). A chloramphenicol-sensitive derivative of BZ24 was designated BZ25. B. subtilis BZ25 has the Npr$^-$ Apr$^-$ phenotype, thus it produces no detectable extracellular neutral protease nor extracellular alkaline protease. Southern blotting was used to confirm the deletion in the aprA gene on the chromosome of B. subtilis BZ25.

Because B. subtilis BZ25 produces no detectable extracellular neutral protease nor subtilisin, it is a useful host strain for introduction of plasmid DNA, such as pAMB113, for the production of mutated subtilisins which may be secreted into the surrounding growth medium free of other proteases.

B. subtilis BZ25 produces no detectable extracellular proteases when culture supernatants are assayed as described below. B. subtilis BZ25/pAMB113, which is BZ25 that harbors plasmid pAMB113 (introduced by the protoplast transformation method of Chang, et al., supra) produces appreciable quantities of [Ser$^{218}$]-subtilisin when culture supernatants are assayed as described.

EXAMPLE 13

Integration of the [Ser$^{218}$]-subtilisin gene into the chromosome of B. subtilis was believed to provide an efficient way of increasing the genetic stability of this mutant gene. Such an approach also alleviates the requirement for chloramphenicol in the fermentation medium which is otherwise needed for application of selective pressure to maintain plasmid DNA in the extrachromosomal state. Therefore, the [Ser$^{218}$]-subtilisin gene, along with its genetic regulatory sequences and flanking DNA homologous to the B. subtilis chromosome, was isolated from a low melting point agarose gel after electrophoresis of pAMB113 which had been digested with EcoRI and PstI in combination. The 4.0 kb EcoRI to PstI fragment (illustrated in FIG. 4) was then ligated to pAMB30 (illustrated in FIG. 5) which had been digested with EcoRI and PstI in combination. Ligation products were introduced into E. coli HB101 (A.T.C.C. 33694) by transformation. Selection was for cells resistant to chloramphenicol (20 μg/ml). Plasmid DNA from four transformants which met the criteria above were isolated by the alkaline extraction procedure of Birnboim, et al., supra, then digested with EcoRI and PstI in combination. All four plasmids contained the 4.0 kb insert and the 5.6 kb remaining portion of pAMB30. One such plasmid, designated pAMB302, was purified and retained for further use.

Repeated attempts to integrate plasmid pAMB302 into the chromosome of B. subtilis BZ25 by the competence method [Spizizen, supra] were unsuccessful. This may have been due to the failure of BZ25 cells to become competent by the method employed. Therefore, pAMB302 was introduced into B. subtilis BZ25 cells by the protoplast transformation method of Chang, et al., supra. This result is particularly significant in that research strains in which integration has been obtained were selected on the basis of transformation by the competence method. Strains which may be unable to become competent, and in particular industrial strains which were not selected on the basis of transformation by the competence method, may be more likely to be unable to become competent.

Selection was for chloramphenicol-resistant cells (5 μg/ml) cells, which were then transferred with sterile toothpicks to L-agar supplemented with 1.5% (w/v) skim milk and 5 μg/ml chloramphenicol. Cells were incubated overnight at 37° C.. Clear halos of different diameters were observed around the Cm$^r$ colonies. This indicates that subtilisin was produced and secreted by these cells. An attempt was made to isolate plasmid DNA from eight of these colonies by the alkaline extraction method. No plasmid DNA was detected on agarose gels which were stained with ethidium bromide (1 μg/ml) to visualize DNA after electrophoresis. The absence of extrachromosomal plasmid DNA in the Cm$^r$ cells which produced subtilisin was a strong indication that pAMB302 had been integrated into the chromosome of B. subtilis.

Several colonies resulting from this experiment were isolated and designated BZ28, BZ29, BZ30, BZ31, BZ32 and BZ33. Each strain was grown overnight at 37° C. with vigorous shaking in brain heart infusion medium (BHI, Difco) supplemented with 5 μg/ml chloramphenicol. Culture supernatants were assayed for subtilisin activity. B. subtilis strains BZ28, BZ29, BZ30, BZ31, BZ32 and BZ33 all produced subtilisin and secreted it into the surrounding growth medium, some strains producing more than others. The amount of subtilisin observed in the liquid culture broth was directly proportional to the size of the halo observed on skim milk L-agar plates. Because of the amounts of subtilisin secreted by these cells differed, multiple copies of pAMB302 were integrated into the chromosome or gene amplification [Young, J. Gen. Microbiol., 129, 1497–1512 (1983); Albertini, et al., J. Bacteriol., 162, 1203–1211 (1985)] had taken place.

EXAMPLE 14

Wild-type subtilisin and subtilisin analogs were isolated and purified as follows. Each culture broth was centrifuged at 15,000 g for 30 minutes and protein in the clear supernatant was precipitated with $(NH_4)_2SO_4$ (600 g per liter). The precipitate was collected by centrifugation, dissolved in 20 mM 2[N-morpholino] ethanesulfonic acid (MES) pH 6.4. The solution was made 30% in acetone, and the 30% acetone supernatant was collected by centrifugation. The supernatant was then made 75% in acetone, and the 30–75% acetone pellet was filtered and dried under vacuum.

In order to further purify the enzyme, the dried precipitate was dissolved in water and the solution was dialyzed against 5 mM MES buffer at pH 6.4. The dialyzed solution was passed through a column (2.5×15 cm) of S-Sepharose FF at a rate of 2 ml per minute. After washing the column with 0.02M MES, the enzyme was eluted with a linear gradient of NaCl in the same buffer, to 0.5M NaCl. Peak fractions were pooled and protein from the fractions containing the enzyme, as identified by a color change in a sample of the fraction mixed with azocasein were dialyzed at 4° C. against 5 mM MES pH 6.3 and then lyophilized.

EXAMPLE 15

Pure subtilisin or subtilisin analog was applied to a Pharmacia FPLC Superose 12 column, and the material eluting as the intact (not cleaved) protein was pooled, in 20 mM MES, 0.1M NaCl, pH 6.4. Samples of wild type subtilisin, or subtilisin analog of the present invention to be evaluated were incubated for 10 min. in the same buffer, the buffer plus 3% SDS, or 20 mM MES, 0.1 M NaCl, 5 mM $CaCl_2$ and 15 mM EDTA at the indicated temperature. The samples were cooled to room temperature for 5 min. and then assayed for 20 min. at room temperature (20° C.) in Tris-HCl, pH 8.0 with 0.6% azocasein to determine proteolytic activity. The proteolytic activity of each sample is expressed as a percentage of the original activity of either wild type or analog, at 20° C. in 10 mM $CaCl_2$, and is represented in Table 2.

TABLE 2

| Temperature | 0% SDS | 3% SDS | 0% SDS + 15 mM EDTA |
|---|---|---|---|
| Proteolytic Activity of Wild Type Subtilisin | | | |
| 20 | 100 | 8 | 100 |
| 35 | 100 | 0 | 62 |
| 50 | 95 | 0 | 37 |
| 70 | 14 | 0 | 14 |
| 100 | 0 | 0 | 0 |
| Activity of [Asp$^{76}$, Ser$^{109}$, Ser$^{218}$] Subtilisin Analog of Example 6 | | | |
| 20 | 100 | 55 | 91 |
| 50 | 100 | 12 | 94 |
| 100 | 5 | 0 | 5 |

EXAMPLE 16

Intact subtilisins were obtained by FPLC on the Superose 12 column. The intact subtilisins were incubated for 30 minutes at room temperature (20° C.) in 15 mM MES, 0.05M NaCl, pH 6.3 containing either 4 mM $CaCl_2$ or 4 mM EDTA, and a varied amount of SDS. The proteolytic activity of the enzyme was then determined by a 20 min. incubation in 0.6% azocasein in Tris-Cl, pH8.0. The proteolytic activity of each sample evaluated is expressed in Table 3 as a percentage of the original activity of the sample in 0% SDS and 10 mM $Ca^{2+}$.

TABLE 3

| % SDS | 4 mM $Ca^{2+}$ | 4 mM EDTA |
|---|---|---|
| Proteolytic Activity of Wild Type Subtilisin | | |
| 0 | 100 | 94 |
| 0.1 | 100 | 76 |
| 0.25 | 100 | 45 |
| 0.50 | 76 | 13 |
| 0.75 | 63 | 3 |
| 1.0 | 60 | 0 |
| 2.0 | 29 | 0 |
| 3.0 | 17 | 0 |
| Proteolytic Activity of [Asp$^{76}$, Ser$^{109}$, Ser$^{218}$] Subtilisin Analog | | |
| 0 | 100 | 95 |
| 0.1 | 100 | 95 |
| 0.25 | 100 | 86 |
| 0.50 | 100 | 81 |
| 0.75 | 96 | 79 |
| 1.0 | 96 | 78 |
| 2.0 | 86 | 69 |
| 3.0 | 71 | 65 |

EXAMPLE 17

For this experiment only the subtilisins were purified as described below.

Each culture broth was centrifuged at 15,000 g for 30 minutes and protein in the clear supernatant was precipitated with $(NH_4)_2SO_4$ (600 g per liter). The precipitate was collected by centrifugation, triturated with 75% acetone, filtered and dried under vacuum.

In order to further purify the enzyme, the dried precipitate was dissolved in water and the solution was filtered and then dialyzed against 0.02M sodium phosphate buffer at pH 6.3. The dialyzed solution was passed through a column (2.5×15 cm) of carboxymethyl cellulose at a rate of 2 ml per minute. After washing the column with 0.02M sodium phosphate (pH 6.3), the enzyme was eluted with the same buffer containing 0.15M NaCl. Peak fractions were pooled and protein from the fractions containing the enzyme, as identified by a color change in a sample of the fraction mixed with succinyl-L-alanyl-L-alanyl-L-prolyl-L-phenylalanyl-p-nitroanilide (Vega Biochemicals), were precipitated by addition of 2.5 volumes of acetone. The precipitate was collected by centrifugation and then dissolved in 0,005M calcium acetate (about 1 ml per 10 mg). The resulting solution was dialyzed at 4° C. against water and then lyophilized.

The stabilities of [Asp$^{76}$, Ser$^{109}$, Ser$^{218}$] subtilisin analog [Asp$^{76}$, Glu$^{79}$, Ser$^{109}$, Ser$^{218}$] subtilisin analog and subtilisin Carlsberg were evaluated at three temperatures (25° C., 37° C. and 50° C.) in two buffer solutions (0.06M sodium phosphate, pH 9.0 or 0.12M sodium glycinate, pH 11.0). The results are expressed in Table 4 as half-life of the enzymes under the specified conditions.

TABLE 4

| Subtilisin | $t_{\frac{1}{2}}$ (25° C.) | $t_{\frac{1}{2}}$ (37° C.) | $t_{\frac{1}{2}}$ (50° C.) |
|---|---|---|---|
| A. In 0.12M sodium glycinate pH 11.0 + 0.2% SDS. | | | |
| [Asp$^{76}$, Ser$^{109}$, Ser$^{218}$] | 110 days | 35.2 hrs | 6.7 hrs |
| analog subtilisin Carlsberg | 2 days | 8.4 hrs | 0.53 hr |
| [Asp$^{76}$, Glu$^{79}$, Ser$^{109}$, Ser$^{218}$] analog | 154 days | 35.3 hrs | 7.8 hrs |
| B. In 0.06M sodium phosphate pH 9.0 + 0.2% SDS. | | | |
| [Asp$^{76}$, Ser$^{109}$, Ser$^{218}$] | 79.2 hrs | 16.0 hrs | 0.52 hr |
| analog subtilisin Carlsberg | 17.3 hrs | 2.4 hrs | 0.18 hr |
| [Asp$^{76}$, Glu$^{79}$, Ser$^{109}$, | 86.3 hrs | 22.0 hrs | 0.96 hr |

TABLE 4-continued

| Subtilisin | t½ (25° C.) | t½ (37° C.) | t½ (50° C.) |
|---|---|---|---|
| Ser$^{2/8}$] analog | | | |
| C. In 0.12M sodium glycinate pH 11.0 + 5 mM EDTA. | | | |
| [Asp$^{76}$, Ser$^{109}$, Ser$^{2/8}$] | 28.7 hrs | 1.87 hrs | 0.25 hr |
| analog subtilisin Carlsberg | 24 hrs | 1.71 hrs | 0.45 hr |
| [Asp$^{76}$, Glu$^{79}$, Ser$^{109}$, Ser$^{2/8}$] analog | 21.5 hrs | 1.42 hrs | 0.20 hr |
| D. In 0.06M sodium phosphate pH 9.0 + 5 Mm EDTA. | | | |
| [Asp$^{76}$, Ser$^{109}$, Ser$^{2/8}$] | 27.4 hrs | 1.75 hrs | 0.23 hr |
| analog subtilisin Carlsberg | 26.3 hrs | 1.68 hrs | 0.32 hr |
| [Asp$^{76}$, Glu$^{79}$, Ser$^{109}$, Ser$^{2/8}$] analog | 19.7 hrs | 1.36 hrs | 0.17 hr |

EXAMPLE 18

Characterization of [Asp$^{76}$, Ser$^{109}$, Ser$^{218}$, Ala$^{222}$]-Subtilisin Analog

[Asp$^{76}$, Ser$^{109}$, Ser$^{218}$, Ala$^{222}$]-subtilisin was purified from *B. subtilis* BZ25/pAMB143 fermentation broth as described in Example 14. The thermal stability, stability in bleach, and specific activity of this subtilisin analog was examined as described below:

I. Thermal Stability

The thermal stability of [Asp$^{76}$, Ser$^{109}$, Ser$^{218}$, Ala$^{222}$]-subtilisin and [Asp$^{76}$, Ser$^{109}$, Ser$^{218}$]-subtilisin and of the wild type enzyme (AprA) were determined using the thermal program of the Gilford Model Response II Spectro-photometer. Samples of purified protease in 20 mM MES, 0.1M NaCl pH 6.3 were heated from 25° C. to 95° C. in the presence of various concentrations of Ca$^{2+}$. The temperature was increased at a rate of 0.5° C. per minute, while following the decrease in absorbance at 287 nm. The melting temperature (Tm) is defined as the temperature where the populations of the unfolded and folded states are equal; in other words, the temperature occurring midway in the transition from folded to unfolded protein. Heat denaturation is an irreversible reaction for subtilisin: in the absence of protease inhibitor the intact enzyme digests the unfolded form, in the presence of inhibitor the protein precipitates as it unfolds. Therefore, the Tm gives us a relative comparison of stability. The melting temperatures determined using this technique are given below.

TABLE 5

| | | Thermal Stability | |
|---|---|---|---|
| mMCa$^{2+}$ | AprA | Tm [Asp$^{76}$, Ser$^{109}$, Ser$^{2/8}$] Subtilisin | [Asp$^{76}$, Ser$^{109}$, Ser$^{2/8}$, Ala$^{222}$]-Subtilisin |
| 0 | 60 | 66 | 66 |
| 1 | 64 | 68 | 68 |
| 5 | 65 | 71 | ND |
| 10 | 66 | 72 | 71 |
| 30 | 68 | 73 | 73 |

ND = not determined

The melting temperatures of the 2 analog subtilisins are very similar at all of the calcium concentrations examined, and are consistently higher than that of the AprA-subtilisin. This indicates that the substitution of Ala for Met at residue 222 did not affect negatively the increased stability and higher calcium binding affinity achieved with the substitutions at positions 76, 109 and 218.

II. Stability in Bleach

Figure 8:
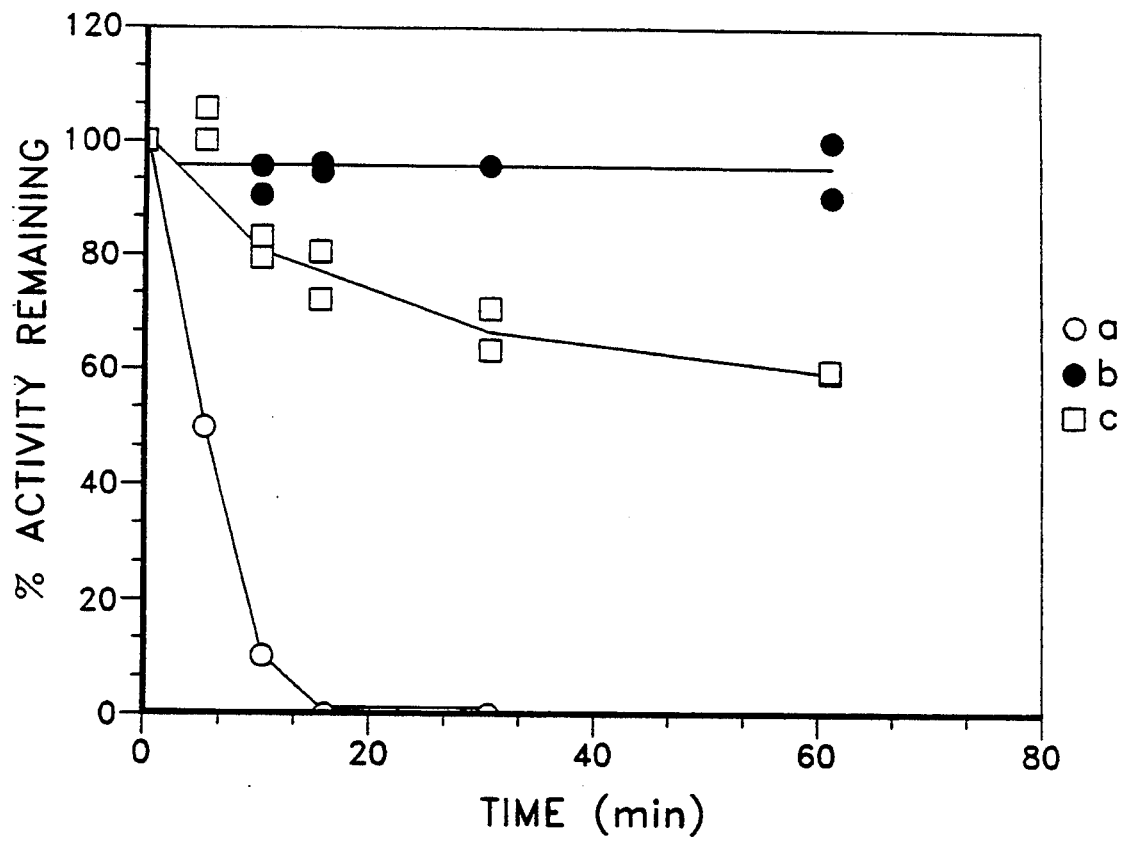
FIG. 8 shows the stability of [Asp$^{76}$, Ser$^{109}$, Ser$^{218}$, Ala$^{222}$] subtilisin in bleach.

As the purpose of removing the Met at position 222 was to decrease the susceptibility of the enzyme to oxidation, the stability of [Asp$^{76}$, Ser$^{109}$, Ser$^{218}$] subtilisin and [Asp$^{76}$, Ser$^{109}$, Ser$^{218}$, Ala$^{222}$]-subtilisin in bleach were compared. In the first experiment, the two analogs were incubated at 50° C., in 20 mM Tris 0.1M NaCl pH 7.5, in the presence of 2% chlorox, 2% chlorox plus 1% SDS, or buffer alone. It should be noted that 2% chlorox bleach is a vast excess compared to the amount normally used by a consumer for laundering fabrics. Aliquots were removed at various times and the protease activity remaining was determined using the azocasein assay. The results are shown in FIG. 8. The activity of both analogs is expressed as percent of activity in the presence of buffer alone, which remained constant throughout the course of the experiment [Asp$^{76}$, Ser$^{109}$, Ser$^{218}$, Ala$^{222}$] retains more activity than [Asp$^{76}$, Ser$^{109}$, Ser$^{218}$] in the presence of 2% bleach, while both analogs appear to lose activity rapidly in the presence of 2% chlorox and 1% SDS, at 50° C.. An interesting observation during this experiment was the fact that under identical conditions, using the same amounts of protein, [Asp$^{76}$, Ser$^{109}$, Ser$^{218}$] had a much higher activity than [Asp$^{76}$, Ser$^{109}$, Ser$^{218}$, Ala$^{222}$]. This will be discussed in more detail below.

The effect of bleach on the structure of [Asp$^{76}$, Ser$^{109}$, Ser$^{218}$, Ala$^{222}$] and [Asp$^{76}$, Ser$^{109}$, Ser$^{218}$] was also assessed using SDS-PAGE. Both analogs were incubated at 50° C. in 20 mM Tris, 0.1M NaCl, 1 mM PMSF, pH 7.5 in the presence of 2% chlorox, or 2% chlorox plus 1% SDS. At different times, 30 μl were removed, mixed with 15 μl of cold (4° C.) sample buffer containing 1 mM PMSF and stored at 4° C. until the experiment was finished. The samples were then subjected to SDS-PAGE on 12.5% polyacrylamide resolving gels. The protein was visualized by staining with Coomassie blue dye, and the amount of intact, folded protein (at the top of the gel), intact, unfolded protein (in the middle of the gel) and proteolytic products (even further down the gel) were quantified using laser densitometry. For analog [Asp$^{76}$, Ser$^{109}$, Ser$^{218}$], after 1 hr in 2% chlorox 45% of the protein remained properly folded, while 2 hr in bleach resulted in all of the protein unfolding, and much of it being digested. For analog [Asp$^{76}$, Ser$^{109}$, Ser$^{218}$, Ala$^{222}$] after 1 hr in bleach, 56% of the protease was still folded, and even following a 2 hr incubation in 2% chlorox at 50° C., 20% of the total protein remained intact. In the 2% bleach, 1% SDS solution the behavior of both analogs was very similar, with 75% still intact and folded after a 5 min incubation, decreasing to 27% of the total protein still folded at 15 min [Asp$^{76}$, Ser$^{109}$, Ser$^{218}$, Ala$^{222}$] does not show greatly increased stability to the combination of denaturants (bleach and SDS) in the concentrations used for this particular assay, but does show enhanced resistance to bleach denaturation.

III. Activity

As mentioned earlier, analog [Asp$^{76}$, Ser$^{109}$, Ser$^{218}$, Ala$^{222}$] has a lower specific activity toward azocasein than analog [Asp$^{76}$, Ser$^{109}$, Ser$^{218}$], with an approximate Vm of 0.02 dA/(min-mg/ml) versus 0.08 dA/(min-mg/ml) for [Asp$^{76}$, Ser$^{109}$, Ser$^{218}$]. To see if this decreased activity was specific for azocasein, or a general characteristic of the [Asp$^{76}$, Ser$^{109}$, Ser$^{218}$, Ala$^{222}$] analog, the kinetics of the hydrolysis of the artificial peptide succinyl Ala-Ala-Pro-Phe-para-nitroanilide was analyzed for [Asp$^{76}$, Ser$^{109}$, Ser$^{218}$, Ala$^{222}$] and [Asp$^{76}$, Set$^{109}$, Ser$^{218}$]. Analog [Asp$^{76}$, Ser$^{109}$, Ser$^{218}$] had a Km of 440 μM and a Vmax of 7.9 dA/(min-nmole); both these values are consistent with those obtained in previous analyses. The Km of [Asp$^{76}$, Ser$^{109}$, Ser$^{218}$, Ala$^{222}$] for the substrate was 1.4 mM, while the Vmax was 1.1 dA/(min-nmole) This represents a three-fold decrease in substrate affinity coupled with a seven-fold decrease in specific activity. This specific activity is 4-fold less than that of aprA-subtilisin. The catalytic Ser is at position 221, and it appears that substitutions at position 222 interfere with substrate binding as well as with the rate limiting step of proteolysis.

EXAMPLE 19

As previously noted in Example 18, [Asp$^{76}$, Ser$^{109}$, Ser$^{218}$, Ala$^{222}$]-subtilisin has a lower specific activity toward azocasein than [Asp$^{76}$, Ser$^{109}$, Ser$^{218}$]-subtilisin and also has a lower specific activity toward the synthetic peptide sAAPFpN substrate. This result is consistent with the loss of activity in the Ala$^{222}$ analog of BPN' subtilisin from *Bacillus amyloliquefaciens* as observed by Estell et al., *J. Biol. Chem.* 260, 6564–6570, 1986. Since casein or azocasein is commonly used as a substrate to determine activity of proteases by manufacturers of detergent enzymes and detergent formulators, the [Asp$^{76}$, Ser$^{109}$, Ser$^{218}$, Ala$^{222}$] subtilisin was not expected to demonstrate improved performance in washing studies performed on soiled fabrics.

Figure 9:
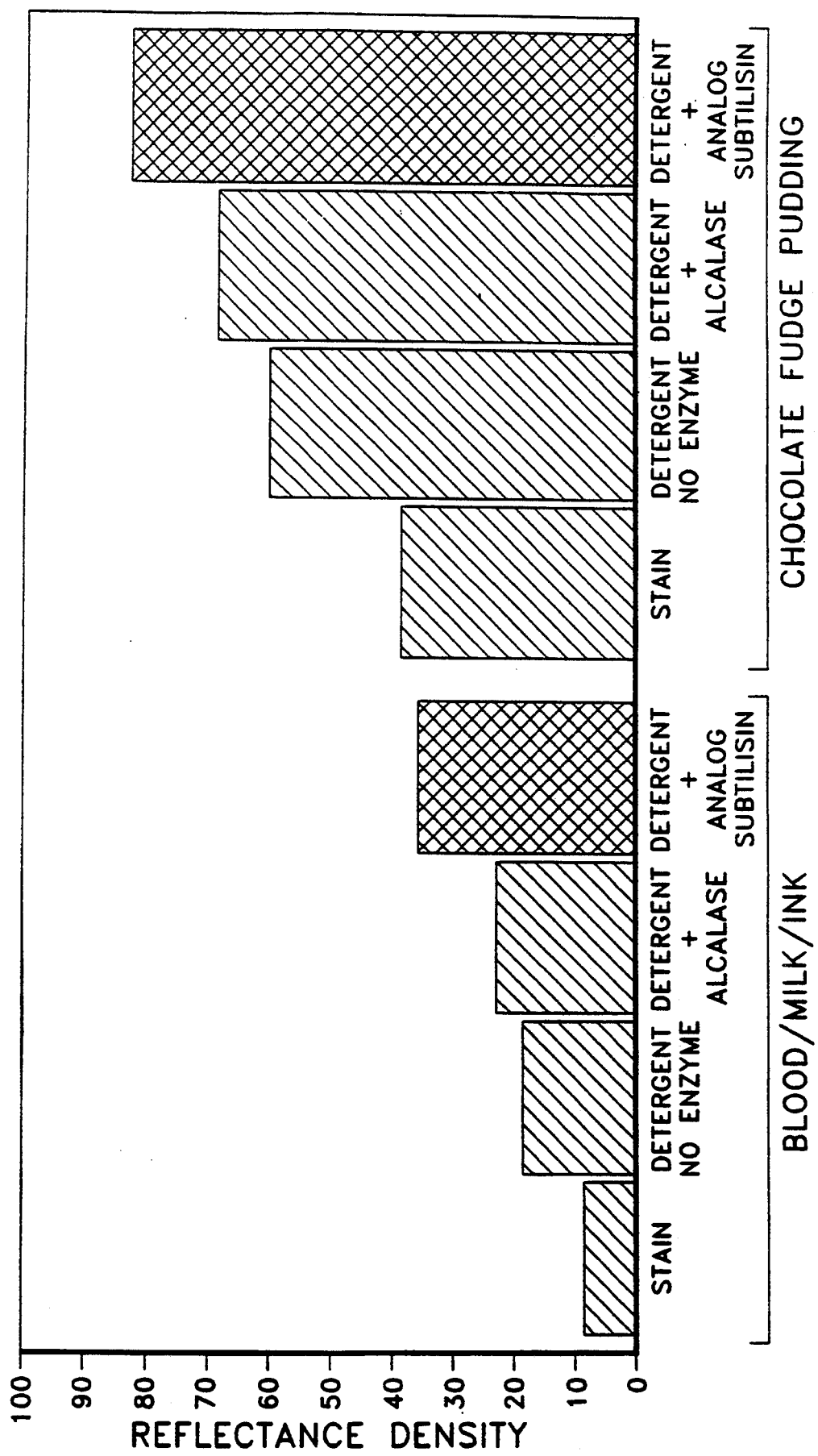

As illustrated in this Example, the [Asp$^{76}$, Ser$^{109}$, Ser$^{218}$, Ala$^{222}$]-subtilisin analog produced the unexpected result of consistently improved performance in removing stains from soiled fabrics under several conditions. The conditions in FIGS. 9 and 10 were as follows:
Whole wash conditions, 10 minute wash
Fresh Start TM with phosphate, pH approx 7 Fresh Start TM without phosphate, pH approx 9
80° and 120° F. wash temperature
150 ppM water hardness
2 stains, 3 swatches each:
  Blood/Milk/Ink (BMI) on cotton
  Chocolate Fudge Pudding (CFP) on a 65% dacron/35% cotton fabric
Controls: 1.5% Alcalase TM in Fresh Start TM 1.5% Termamyl TM in Fresh Start TM
Enzymes tested at equivalent activities based on azocasein units/ml for protease and dinitrosalicylic acid units/ml for amylase.

The legend for FIG. 10 is as follows:

| CONDITIONS | DETERGENT TYPE | TEMPERATURE | STAIN |
|---|---|---|---|
| A | Nonphosphate | 80° F. | Blood/Milk/Ink |
| B | Nonphosphate | 80° F. | Chocolate Fudge Pudding |
| C | Nonphosphate | 120° F. | Blood/Milk/Ink |
| D | Nonphosphate | 120° F. | Chocolate Fudge Pudding |
| E | Phosphate | 80° F. | Blood/Milk/Ink |
| F | Phosphate | 80° F. | Chocolate Fudge Pudding |
| G | Phosphate | 120° F. | Blood/Milk/Ink |
| H | Phosphate | 120° F. | Chocolate Fudge Pudding |

Even when the amount of [Asp$^{76}$, Ser$^{109}$, Ser$^{218}$, Ala$^{222}$]-subtilisin was used at one-third of the activity as the Novo Alcalase control, the analog of the present invention was still superior in performance in Table 6.

TABLE 6

Washing Machine Evaluation Of [ASP$^{76}$, Ser$^{109}$, Ser$^{218}$, Ala$^{222}$]-Subtilisin Phosphate-Containing Fresh Start TM at 100° F.

| | Total delta Rd | |
|---|---|---|
| | Novo | 143 |
| Without Ballast* | 72.6 | 76.6 |
| With Ballast | 44.0 | 56.4 |
| Total Rd Loss Due to Ballast | 28.6 | 20.2 |

Novo used at 9 azo/L while 143 used at only 3 azo/L
*Ballast refers to additional soiled clothing that was added to the washing machine in addition to soiled swatches of fabric.

While the present invention has been described in terms of preferred embodiments it is understood that modifications and improvements will occur to those skilled in the art. Thus, it is expected that substitution of residues at calcium binding sites other than at the specific calcium described herein may improve stability as well. Additional improvements in stability are expected for such substitutions made in other enzymes which have the Asn-Gly sequence and in other proteins comprising this sequence. Additional improvements in specific activity for such substitutions made in other enzymes when modifications of amino acids surrounding the active site amino acids are incorporated into the protein. Whereas each single substitution may improve the stability, calcium binding or specific activity of the enzyme, the combination of several modifications in one enzyme is required to produce an enzyme for commercial applications. Furthermore, because each amino acid substitution alters the primary structure of the enzyme and may affect neighboring amino acid residues through electrostatic effects, hydrogen bonding, etc., the combination of substitutions may not always produce an additive and incremental improvement to the enzyme. The correct combinations according to the present invention produce subtilisins with superior properties. Furthermore, it is expected that a subtilisin analog according to the present invention possesses superior properties to wild type subtilisins in detergent formulations such as those disclosed in, for example, U.S. Pat. Nos. 3,732,170; 3,749,671 and 3,790,482, all of which are incorporated by reference herein.

Moreover, for practical reasons many industrial processes are conducted at temperatures that are above the stability temperature range of most enzymes. Therefore, although detergent applications have been emphasized herein, it is believed that subtilisin analogs according to the present invention are not only advantageous to certain industries such as detergent industry, which already require stable subtilisins, but also may be useful in industries that use chemical means to hydrolyze proteins, e.g. hydrolysis of vegetable and animal proteins.

Therefore, it is intended that the present invention include all such modifications and improvements as come within the scope of the present invention as claimed.

What is claimed is:

1. A substantially pure subtilisin characterized as having improved pH, thermal, and oxidative stability, and increased specific activity, the subtilisin comprising an amino acid sequence of a naturally occurring Bacillus subtilisin that has been modified by having:
  (1) from one to five of the amino acids selected from the group consisting of Pro$^{14}$, Asp$^{41}$, Leu$^{75}$, Asn$^{76}$, Asn$^{77}$, Ser$^{78}$, Ile$^{79}$, Gly$^{80}$, Val$^{81}$, Asp$^{140}$, Pro$^{172}$ Thr$^{208}$, Tyr$^{214}$, and Gln$^{271}$ replaced by Asp or Glu; and (2) one or more amino acids of an Asn-Gly sequence deleted or replaced by a different amino acid; and (3) neither, either or both Met$^{124}$ and Met$^{222}$ replaced with Ala or Leu; and (4) Arg$^{247}$ replaced with Leu or Met, wherein the numbering which designates sites for modifications is that of the following mature Bacillus subtilisin amino acid sequence:

```
 1               5              10             15
Ala Gln Ser Val Pro Tyr Gly Ile Ser Gln Ile Lys Ala Pro Ala 20             25             30
Leu His Ser Gln Gly Tyr Thr Gly Ser Asn Val Lys Val Ala Val 35             40             45
Ile Asp Ser Gly Ile Asp Ser Ser His Pro Asp Leu Asn Val Arg 50             55             60
Gly Gly Ala Ser Phe Val Pro Ser Glu Thr Asn Pro Tyr Gln Asp 65             70             75
Gly Ser Ser His Gly Thr His Val Ala Gly Thr Ile Ala Ala Leu 80             85             90
Asn Asn Ser Ile Gly Val Leu Gly Val Ala Pro Ser Ala Ser Leu 95            100            105
Tyr Ala Val Lys Val Leu Asp Ser Thr Gly Ser Gly Gln Tyr Ser 110            115            120
Trp Ile Ile Asn Gly Ile Glu Trp Ala Ile Ser Asn Asn Met Asp 125            130            135
Val Ile Asn Met Ser Leu Gly Gly Pro Thr Gly Ser Thr Ala Leu 140            145            150
Lys Thr Val Val Asp Lys Ala Val Ser Ser Gly Ile Val Val Ala 155            160            165
Ala Ala Ala Gly Asn Glu Gly Ser Ser Gly Ser Thr Ser Thr Val 170            175            180
Gly Tyr Pro Ala Lys Tyr Pro Ser Thr Ile Ala Val Gly Ala Val 185            190            195
Asn Ser Ser Asn Gln Arg Ala Ser Phe Ser Ser Ala Gly Ser Glu 200            205            210
Leu Asp Val Met Ala Pro Gly Val Ser Ile Gln Ser Thr Leu Pro 215            220            225
Gly Gly Thr Tyr Gly Ala Tyr Asn Gly Thr Ser Met Ala Thr Pro 230            235            240
His Val Ala Gly Ala Ala Ala Leu Ile Leu Ser Lys His Pro Thr 245            250            255
Trp Thr Asn Ala Gln Val Arg Asp Arg Leu Glu Ser Thr Ala Thr 260            265            270
Tyr Leu Gly Asn Ser Phe Tyr Tyr Gly Lys Gly Leu Ile Asn Val

275
Gln Ala Ala Ala Gln.
```

2. A subtilisin according to claim 1 which is a Bacillus subtilisin selected from the group consisting of subtilisin Carlsberg, subtilisin DY, subtilisin BPN', an aprA subtilisin of *Bacillus subtilis* and subtilisin from *Bacillus mesentericus*.

3. A subtilisin according to claim 1 having Asn$^{76}$ replaced with Asp$^{76}$.

4. A subtilisin according to claim 1 having Ile$^{79}$ replaced with Gly$^{79}$.

5. A subtilisin according to claim 1 having Asn$^{76}$ replaced with Asp$^{76}$ and Ile$^{79}$ replaced with Glu$^{79}$.

6. A subtilisin according to claim 1 wherein Met$^{222}$ is replaced by Ala.

7. A subtilisin according to claim 1 wherein Met$^{124}$ replaced by Leu or Ala.

8. A subtilisin according to claim 1 selected from the group consisting of Asp$^{76}$/Ser$^{109}$/Ser$^{218}$/Ala$^{222}$/Met$^{247}$ subtilisin and Asp$^{76}$/Ser$^{109}$/Ser$^{218}$/Ala$^{222}$/Leu$^{247}$ subtilisin.

9. A subtilisin according to claim 1 selected from the group consisting of Leu$^{31}$/Asp$^{76}$/Ser$^{109}$/Ser$^{218}$/Ala$^{222}$/Met$^{247}$ subtilisin, Leu$^{31}$/Asp$^{76}$/Ser$^{109}$/Ser$^{218}$/Ala$^{222}$/Leu$^{247}$ subtilisin, Asp$^{76}$/Ser$^{109}$/Leu$^{124}$/Ser$^{218}$/Ala$^{222}$/Met$^{247}$ subtilisin, Asp$^{76}$/Ser$^{109}$/Leu$^{124}$/Ser$^{218}$/Ala$^{222}$/Leu$^{247}$ subtilisin, Asp$^{76}$/Ser$^{109}$/Ala$^{124}$/Ser$^{218}$/Ala$^{222}$/Met$^{247}$ subtilisin, and Asp$^{76}$/Ser$^{109}$/Ala$^{124}$/Ser$^{218}$/Ala$^{222}$/Leu$^{247}$ subtilisin.

10. A subtilisin according to claim 1 wherein an Asn residue in the Asn-Gly sequence is replaced by a residue of a different amino acid.

11. The subtilisin as recited in claim 10 wherein an Asn residue in the Asn-Gly sequence is replaced by a residue of an amino acid selected from the group consisting of Ser, Val, Thr, Cys, Glu and Ile.

12. A subtilisin according to claim 11 wherein the Asn residue in the Asn-Gly sequence is replaced by Ser.

13. A subtilisin according to claim 12 wherein an Asn residue at position 109 is replaced by Ser.

14. A subtilisin according to claim 12 wherein an Asn residue at position 218 is replaced by Ser.

15. A subtilisin according to claim 12 wherein an Asn residue at positions 109 and 218 is replaced by Ser.

16. A subtilisin according to claim 15 selected from the group consisting of Asp$^{76}$/Ser$^{109}$/Ser$^{218}$/Met$^{247}$ subtilisin, Asp$^{76}$/Ser$^{109}$/Ser$^{218}$/Leu$^{247}$ subtilisin, Glu$^{76}$/Ser$^{109}$/Ser$^{218}$/Met$^{247}$ subtilisin, Glu$^{79}$/Ser$^{109}$/Ser$^{218}$/Leu$^{247}$ subtilisin, Asp$^{76}$/Glu$^{79}$/Ser$^{109}$/Ser$^{218}$/Met$^{247}$ subtilisin, and Asp$^{76}$/Glu$^{79}$/Ser$^{109}$/Ser$^{218}$/Leu$^{247}$ subtilisin.

17. A composition comprising an effective amount of a subtilisin of claim 1 in a detergent formulation.

* * * * *